("12") United States Patent  
Goldstein et al.

(10) Patent No.: US 7,544,468 B2
(45) Date of Patent: Jun. 9, 2009

(54) SIMULTANEOUS COLLECTION OF DNA AND NON-NUCLEIC ANALYTES

(75) Inventors: Andrew S. Goldstein, Portland, OR (US); Richard K. Bestwick, Portland, OR (US)

(73) Assignee: Orasure Technologies, Inc., Bethlehem, PA (US)

( * ) Notice: Subject to any disclaimer, the term of this patent is extended or adjusted under 35 U.S.C. 154(b) by 1149 days.

(21) Appl. No.: 09/983,735

(22) Filed: Oct. 25, 2001

(65) Prior Publication Data

US 2002/0115089 A1    Aug. 22, 2002

Related U.S. Application Data

(62) Division of application No. 09/049,714, filed on Mar. 27, 1998, now Pat. No. 6,309,827.

(60) Provisional application No. 60/042,124, filed on Mar. 28, 1997.

(51) Int. Cl.
    *C12Q 1/68* (2006.01)
(52) U.S. Cl. .......................................... 435/6; 424/550
(58) Field of Classification Search .................... 435/6, 435/5, 4, 7.9; 424/484, 486, 550
    See application file for complete search history.

(56) References Cited

U.S. PATENT DOCUMENTS

| | | | | |
|---|---|---|---|---|
| 4,921,787 | A | 5/1990 | Riggin et al. | 435/5 |
| 5,022,409 | A | 6/1991 | Goldstein et al. | 128/760 |
| 5,103,836 | A | 4/1992 | Goldstein et al. | 128/760 |
| 5,112,758 | A | 5/1992 | Fellman et al. | 436/8 |
| 5,120,643 | A | 6/1992 | Ching et al. | 435/7.92 |
| 5,188,968 | A | 2/1993 | Kano et al. | 436/501 |
| 5,209,904 | A | 5/1993 | Forney et al. | 422/73 |
| 5,234,001 | A | 8/1993 | Goldstein et al. | 128/760 |
| 5,335,673 | A | 8/1994 | Goldstein et al. | 128/760 |
| 5,339,829 | A | 8/1994 | Thieme et al. | 128/760 |
| 5,413,913 | A | 5/1995 | Hillyard et al. | 435/7.25 |
| 5,479,937 | A | 1/1996 | Thieme et al. | 128/760 |
| 6,322,983 | B1 * | 11/2001 | Burgoyne | 435/6 |

FOREIGN PATENT DOCUMENTS

| | | | |
|---|---|---|---|
| EP | 0323605 | B1 | 1/1994 |
| EP | 0 591 914 | | 4/1994 |
| EP | 0591914 | A2 | 4/1994 |
| GB | 2204398 | A | 11/1988 |
| WO | WO 91/13355 | | 9/1991 |
| WO | WO 92/16842 | | 10/1992 |
| WO | WO 93/08474 | | 4/1993 |

OTHER PUBLICATIONS

Thomson et al. "Routine use of hair root or buccal swab specimens for PCR analysis: Advantages over using blood" Clinica Chimica Acta, vol. 207, Issue 3, pp. 169-174, May 15, 1992.*
Holm-Hansen et al. 2004; Comparison of oral fluid collectors for use in a rapid point-of-care diagnostic device. Clinical and Diagnostic Laboratory Immunology 11 (5): p. 909-912.*
H.A. John et al., "RNA-DNA hybrids at the Cytological Level," Nature 223:582-587 (Aug. 9, 1969).
Margaret L.M. Anderson et al., "Nucleic Acid Hybridisation", Chapter 4:73-111, IRL Press, Oxford 1985.
David W. Archibald et al., "Salivary Antibodies as a Means of Detecting Human T Cell Lmphotrophic Virus Type III/Lymphadenopathy-Associated Virus Infection," *J. Clin. Micro.* 24(5):873-875 (Nov. 1986).
J.V. Parry et al., "Sensitive Assays For Viral Antibodies In Saliva; An Alternative To Tests On Serum," *The Lancet*: 72-75, Jul. 11, 1987.
Edward J. Cone et al., "Saliva Testing For Drugs of Abuse" vol. 694:91-127, Presented at the N.Y. Acad, Sciences, Oct. 22, 1992-Oct. 25, 1992.
John V. Parry "Simple and Reliable Salivary Tests For HIV and Hepatitis A and B Virus Diagnosis and Surveillance," 694:216-233, *Saliva As A Diagnostic Fluid, Ann. New York Acad. Sci.*, Malamud and Tabak, eds., N.Y. Acad. Sci. Pub. (1993).
Brenda Richards et al., "Multiplex PCR Amplification From The CFTR Gene Using DNA Prepared From Buccal Brushes/Swabs," *Human Molecular Genetics* 2(2):159-163 (1993).
Michael H. Irwin et al., "Identification Of Transgenic Mice By PCR Analysis of Saliva" *Nature Biotechnology* 14:1146-1148 (Sep. 1996).

\* cited by examiner

*Primary Examiner*—Karen Cochrane Carlson

(57) ABSTRACT

This invention provides for a rapid and convenient method of simultaneous collection of both genomic and diagnostic information from a single sample on a bibulous pad by differential extraction of the diagnostic information from the genomic information. It is a surprising discovery of this invention that a PCR assay on the contents of the bibulous pad provides results comparable in reliability, specificity, and sensitivity to the best available serum (blood) based assays. The assays of this invention can be used to confirm each other, either by detecting the genomic information leading to the diagnostic information, or by detecting in the genomic information, a predisposition to a disease and confirming the presence of the disease through diagnostic testing.

23 Claims, 6 Drawing Sheets

9 10 11 13 14 15 16 17 19 20   21 22 23 24 25 26 27 28

1  2  3  4  5 CTRL 6  7  8  9 10 11   13 14 15 16 17  19 20 21 22 23

SEQ ID NO:1 5'-GGCTGTGTTTGCGTCTCTCC-3' (GenBank Accession No. U57840:491U20)

SEQ ID NO:2 5'-GACCAGCCCCAAGATGACTATC-3' (GenBank Accession No. U57840:617122)

*FIG. 6.*

SIMULTANEOUS COLLECTION OF DNA AND NON-NUCLEIC ANALYTES

CROSS-REFERENCE TO RELATED APPLICATIONS

This application is a divisional of U.S. application Ser. No. 09/049,714, filed on Mar. 27, 1998, now U.S. Pat. Ser. No. 6,309,827, which is herein incorporated by reference in its entirety, which claims priority to U.S. Provisional Application No. 60/042,124, filed Mar. 28, 1997.

FEDERALLY SPONSORED RESEARCH AND DEVELOPMENT

Not Applicable

BACKGROUND OF THE INVENTION

Currently, most analyte and DNA diagnostic assays are blood-based. Blood-based testing is invasive and poses a significant safety hazard. An alternate procedure, collecting lymph fluid, often involves surgically draining or removing lymph nodes. Collecting vaginal, rectal and nasal fluids is inconvenient and can be uncomfortable and embarrassing for both the medical professional and the patient. In contrast, the collection of oral fluid including saliva and/or mucosal transudate for testing entails minimal invasion of privacy, is convenient, relatively safe, and can be accomplished rapidly with ease. In addition, in patients where only small volumes of blood can be drawn, for example, newborns and the elderly, adequate volumes for testing can be obtained from saliva or mucosal transudate.

The idea for using oral fluid in a detection method has been discussed in scientific and clinical research for some time. Researchers have investigated using oral fluid as a possible clinical specimen for diagnosis of specific disease states or altered metabolic activity (see, e.g., *Ann. New York Acad. Sci., Vol. 694: Saliva as a Diagnostic Fluid*, Malamud and Tabak, eds., N.Y. Acad. Sci. Pub. (1993)). Moreover, studies have shown that antibodies have been detected in saliva samples (Archibald et al. *J Clin Micro.* 24:873-875 (1986); Parry et al. *Lancet* 2:72-75 (1987)).

A number of enzyme immunoassay (EIA) kits are currently available for the screening of serum (blood) specimens for antibodies. An FDA approved EIA kit is also available specifically for screening oral fluid specimens (in particular oral fluid specimens collected using the ORASURE® HIV-1 oral specimen collection device).

Detection of nucleic acid sequences in oral fluids by polymerase chain reaction (PCR) amplification and then visualization through agarose gel electrophoresis or blotting techniques has also been described (see, e.g., Irwin, et al, *Nature Biotechnology* 14:1146-8 (1996); Richards, et al., *Human Molecular Genetics* 2(2):159-63 (1993)). However, the literature describes using saliva or buccal cells from scraping or brushing the inside of the cheek.

The simultaneous collection of an oral fluid sample which is the basis of diagnostic and genomic assays has not hithertofore been described. Simultaneous collection would be useful when screening assay results must be confirmed in another type of assay, i.e., an HIV test. Simultaneous collection would also be useful to diagnose two or more different pathological conditions by different assays. Instead of having to collect two samples of biological fluid; the investigator could collect one sample and run the necessary assays on that sample. Finally, simultaneous collection by a single device would be useful for the detection of genetic markers demonstrating a predisposition to a certain disease and the detection of the diagnostic markers indicating the presence of that disease.

In the present invention, a bibulous pad is used to collect oral fluids. This technique has proven to be better than the methods described in the prior art which involve collecting cells with buccal brushes and swabs (Richards, et al., supra) which can be painful and oral rinses with distilled water or saline (Irwin, et al., supra). Both of these methods produce a lower yield of nucleic acids and nucleic acids of lower quality than the methods and systems claimed below.

In the present invention, an absorbent pad is contacted with oral fluid. The fluid is expressed from the pad and assayed for the presence of diagnostic marker, including immunological markers and drug and drug metabolites. A surprisingly pure and stable preparation of genomic DNA is then extracted from the pad. The exceptional purity of the DNA is not fully understood but may be due to the preservative solution used to store the pad or the pad may preferentially bind DNA or cells which contain the genomic DNA.

SUMMARY OF THE INVENTION

This invention provides for a rapid and convenient method of simultaneous collection of both genomic and diagnostic information from a single sample on a bibulous pad by differential extraction of the diagnostic information from the genomic information. The diagnostic information is physically extracted from the pad on which the genomic information remains. The genomic information is released from the pad under conditions suitable to lyse whole cells and release genomic DNA from the bibulous pad. It is a surprising discovery of this invention that a PCR assay on the contents of the bibulous pad provides results comparable in reliability, specificity, and sensitivity to the best available serum (blood) based assays.

The solution used to release the genomic information comprises a low concentration of buffer salts with buffering capacity of pH 6-9, a chelating agent, a non-ionic detergent, an antimicrobial agent and a proteinase. Alternatively, chaotropic agents may be used to release the genomic information or the nucleic acids can be separated from the pads by mechanical means, including sonication or shearing.

The assays of this invention can be used to confirm each other, either by detecting the genomic information leading to the diagnostic information, or by detecting in the genomic information, a predisposition to a disease and confirming the presence of the disease through diagnostic testing.

This invention also encompasses a system for differentially extracting diagnostic information from genomic information from the same bibulous pad. Preferably, the system incorporates an identification system so the extracts are identified as originating from the same source. The system can be incorporated into a kit with instructions for use. The kit optionally comprises means for holding the extracts. Preferably the means is sealable so a chain of custody from source of the biological fluid to practitioner assaying the fluid is established.

BRIEF DESCRIPTION OF THE DRAWINGS

FIG. 6 is the SEQ ID NO: listings for the PCR primers used to amplify CKR5 gene fragments.

DEFINITIONS

Figure 1:
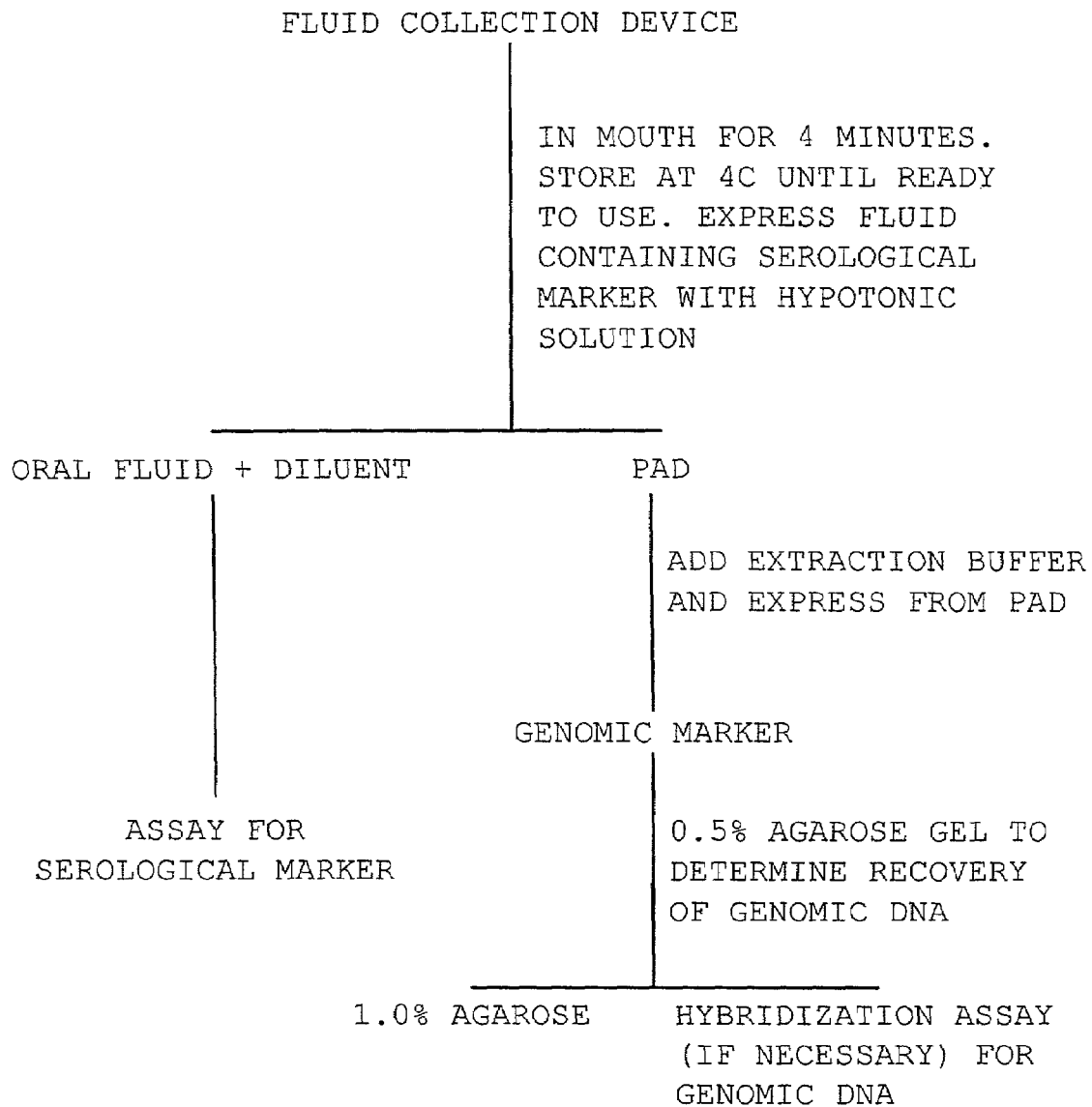
FIG. 1 illustrates the recommended testing algorithm for simultaneous oral fluid antibody and DNA specimens.

The term "AIO" or "anti-infectious oral sample" refers to an oral sample to be assayed for the presence of anti-microbial drugs. These drugs include antibiotics, such as penicillin, Bactrim, ciprofloxacin vancomycin, gentamicin and others used to treat bacterial infections. Also included are drugs used to treat tuberculosis, such as isoniazid and rifampin. Anti-microbial drugs also include anti-viral drugs, such as nucleoside analogs and protease inhibitors. Also included are anti-fungal and anti-protozoal drugs.

The term "amplification" refers to methods used to increase the number of specific nucleic acid sequences. Suitable amplification methods include, but are not limited to PCR, ligase chain reaction (LCR) (see, Wu and Wallace, *Genomics*, 4: 560 (1989); Landegren et al., *Science*, 241:1077 (1988); and Barringer et al., *Gene*, 89:117 (1990); transcription amplification (Kwoh et al., *Proc. Natl. Acad. Sci. USA*, 86:1173 (1989)); and self-sustained sequence replication (Guatelli, et al., *Proc. Nat. Acad. Sci. USA*, 87:1874 (1990)).

The term "agarose gel electrophoresis" refers to agarose gel electrophoresis wherein nucleic acid migrates into an agarose gel as electrical current is applied to the gel. The nucleic acid, because of its equal ionic charge, migrates according to its size.

As used herein, the term "antibody" refers to intact immunoglobulins as well as various forms of modified or altered antibodies produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond (Bird et al., *Science* 242:424 (1988); Huston et al., *Proc. Nat. Acad. Sci. USA* 85:5879 (1988)). The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region. The Fv region is the variable part of Fab; a $V_H$-$V_L$ dimer (Brinkmann, et al, *Proc. Natl. Acad. Sci. USA*, 90:547 (1993)). See, FUNDAMENTAL IMMUNOLOGY, W. E. Paul, ed., Raven Press, N.Y. (1993), for a more detailed description of other antibody fragments.

While various antibody fragments are defined in terms of the digestion of an intact antibody, one of skill will appreciate that such fragments (e.g., Fv) may be synthesized de novo either chemically or by utilizing recombinant DNA methodology. Thus, the term antibody, as used herein also includes antibody fragments either produced by the modification of whole antibodies or synthesized de novo using recombinant DNA methodologies.

The term "assay diluent" refers to a solution that dilutes the diagnostic marker releasing solution (DMRS) prior to assay. While most assay buffers can be used (See, e.g., CURRENT PROTOCOLS IN IMMUNOLOGY Wiley/Greene, N.Y.; Harlow and Lane (1989); ANTIBODIES: A LABORATORY MANUAL, Cold Spring Harbor Press, N.Y.; Stites et al. (eds.) BASIC AND CLINICAL IMMUNOLOGY (4TH ED.) Lange Medical Publications, Los Altos, Calif., and references cited therein), particularly preferred assay diluents comprise buffering salts, including Tris, carbonate, phosphate, borate, citrate, HEPES, etc.; sodium or another alkali salt and a preservative to prevent microbial growth. Particularly preferred assay diluents have an effective buffering capacity of between about pH 7 to about pH 9, more preferably from about pH 7.5 to about pH 8.5, and most preferably around pH 8. In a particularly preferred embodiment, the assay diluent comprises from 0.05 to 0.2 M $NaHCO_3$, pH 8.0, preferably 0.1 M. A preferred preservative is thimerosal at a concentration of from 0.005-0.1%, most preferably about 0.01%.

The phrase "bar code" refers to a series of contiguous lines of like height coded by width and applied to an item for identification by an optical scanner.

The phrase "binding specificity", "specifically binds to an antibody" or "specifically immunoreactive with," when referring to an analyte, refers to a binding reaction which is determinative of the presence of the analyte in the presence of a heterogeneous population of proteins and other biologics. Thus, under designated immunoassay conditions, the specified antibodies bind to a particular analyte and do not bind in a significant amount to other compounds present in the sample.

The term "cannabinoids" refers to organic substances present in *Cannabis sativa*, having a variety of pharmacologic properties. Cannabinoids include tetrahydrocannabinol (THC), cannabinol, and cannabidiol. For purposes of this invention, cannabinoids also include the metabolites of cannabinoids, including but not limited to, $\Delta^9$-THC, L-9-carboxy-11-nor-$\Delta^9$-THC glucuronide, 11-nor-9-carboxy-THC and $\Delta^8$-THC.

The term "cellular components" refers to the parts of a cell. It includes the cellular membrane and the cell contents within the cell membrane of an intact cell.

The term "cocaine" refers to the psychotropic drug benzoylmethylecgonine. For purposes of this invention, cocaine also refers to its metabolites, including but not limited to, ecgonine methyl ester (EME), benzoylecgonine (BE), ecgonine and cocaethylene.

The phrases "DAO" or "drugs of abuse oral sample" refers to an oral sample to be assayed for the presence of drugs of abuse. Drugs of abuse refer to pharmacological compounds that are typically abused. This class of drugs includes, but is not limited to, cannabinoids, cocaine, methamphetamine, amphetamine, barbituates, opiates, including heroin and morphine, and hallucinogens, such as lysergic acid diethylamide phencyclidine and mescaline.

The phrases "DMO" and "disease markers oral sample" refers to a biological fluid sample that is to be assayed for a disease that is diagnosed by the presence of a compound that is not normally present in the non-disease state. For example, prostate cancer is detected by the presence of PSA. C-reactive protein is present in measurable quantities during acute inflammation. Antigen-specific immunoglobulins are present in response to the release of foreign immunogens. In addition to the presence of a compound, the absence of a compound normally present in the non-disease state can be used to diagnose a disease. For example, the lack of thyroxin indicates hypothyroidism and the absence of glucose indicates hypoglycemia. Other disease markers presently known to those of skill and disease markers that will be known in the future are encompassed by this invention.

The term "extracellular analytes" refers to diagnostic markers found within a mammalian body but not within cells. It includes compounds secreted by cells, such as antibodies and compounds which are the result of metabolic reactions within the body but not incorporated into cells, such as cholesterol, cotinine and other drug metabolites. Extracellular analytes also include deleterious extracellular analytes which inhibit or interfere with genomic analysis.

The term "genomic analysis" refers to assays performed on genomic DNA. These assays include but are not exclusive of PCR, LCR, nuclear run-on assays, chromosome walking, nucleotide sequencing, and hybridization techniques.

The term "genomic marker" refers to a segment of genomic DNA that can be isolated and amplified if necessary to identify a certain individual or genotype.

The term "hybridization probe" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett*. 22:1859 (1981), or by the triester method according to Matteucci, et al., *J. Am. Chem. Soc*. 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The term "hypertonic solution" refers to a solution that impregnates the collection pad. The solution comprises a salt solution with an ionic strength greater than that of blood. The solution may contain saliva stimulators, such as weak organic acids, preservatives, such as bacteriostatic agents and protease inhibitors, and blocking agents, such as bovine gelatin and non-ionic detergents, such as TWEEN-20®.

The phrase "identification system" refers to a method of labeling each component that comprises a system of this invention to identify the source of the biological fluid contained within the component. For example, the collection and specimen tubes into which the extracts from the bibulous solid support are stored are labeled with identical bar codes.

The term "immunoassay" refers to an assay wherein a target compound binds specifically with an antibody. Specific binding to an antibody requires an antibody that is selected for its specificity for a particular analyte. As described below, a variety of immunoassay formats may be used to select antibodies specifically immunoreactive with a particular analyte. For example, solid-phase ELISA immunoassays are routinely used to select monoclonal antibodies specifically immunoreactive with an analyte. See, Harlow and Lane (1988) ANTIBODIES, A LABORATORY MANUAL, Cold Spring Harbor Publications, New York ("Harlow and Lane"), for a description of immunoassay formats and conditions that can be used to determine specific immunoreactivity. Typically a specific or selective reaction will be at least twice background signal or noise and more typically more than 10 to 100 times background.

The term "labeled antibody" as used herein refers to an antibody, or antibody fragment, bound to a label such that detection of the presence of the label (e.g., as bound to an antibody) indicates the presence of the analyte to which the antibody binds.

The phrase "means for holding extract" refers to a container intended to hold an aqueous extract removed from the bibulous solid support. The container may be, for example, a test tube, a centrifuge tube, a well of a microtiter plate, or a plastic bag or bottle. The only requirement is that it be capable of holding the aqueous extract and is impervious to other solutions that are in contact with the outside of the container.

The term "metabolites" refers to any product of a biochemical reaction in living tissues. Metabolites include the product of a biochemical reaction in which a substrate is a non-nucleic acid analyte, such as drugs, proteins, carbohydrates, and lipids.

The term "methamphetamine" refers to the drug methylamphetamine hydrochloride; a sympathomimetic agent that exerts a stimulating effect upon the central nervous system. For purposes of this invention, methamphetamine also includes its metabolites.

The term "mucosal transudate", as used herein, refers to fluid produced by the passive diffusion of serum components from oral mucosal interstitia into the oral cavity and often forms one component of saliva.

The term "nucleic acid" includes all types of nucleic acids, including but not limited to genomic and specific sequences of DNA and RNA.

The term "nucleic acid releasing solution (NARS)" means a buffer that can be used to extract nucleic acids from the pad on the oral collection device. This buffer preferably comprises a low concentration of buffering salts with an effective buffering capacity of about pH 6-pH 9, a chelating agent and a detergent. A particularly preferred nucleic acid extraction buffer contains but is not limited to 10 mM Tris, 0.1 M EDTA, and 0.5% SDS.

The term "oral fluid", as used herein, refers to one or more fluids found in the oral cavity individually or in combination. These include, but are not limited to salivary secretions and mucosal transudate. It is recognized that oral fluid (e.g., saliva) can comprise a combination of fluids from a number of sources (e.g., parotid, submandibular, sublingual, accessory glands, gingival mucosa and buccal mucosa) and the term oral fluid includes the fluids from each of these sources individually, or in combination. The term saliva refers to a combination of oral fluids such as is typically found in the mouth, in particular after chewing.

The term "ORASURE® sample or specimen" refers to an oral fluid sample collected using the ORASURE® oral fluid collection device. Oral fluid samples obtained using the ORASURE® device typically show an increased concentration of mucosal transudate and a higher antibody concentration as compared to saliva.

The term "ORAQUICK® sample or specimen" refers to an oral fluid sample collected using the ORAQUICK® oral fluid collection device. Oral fluid samples obtained using the ORAQUICK® device typically show an increased concentration of mucosal transudate and a higher antibody concentration as compared to saliva.

The term "PCR" means the amplification of nucleic acid sequences by incubating nucleic acid with specific primers and a DNA polymerase and alternating the temperature of the incubation such that the primers bind to single stranded nucleic acid, the DNA polymerase creates a complementary strand to the single strand of nucleic acid, and the two strands separate to allow for new binding of primers.

Various methods of amplifying target sequences, such as PCR, can also be used to prepare DNA. In PCR techniques, oligonucleotide primers complementary to the two 3' borders of the DNA region to be amplified are synthesized. The polymerase chain reaction is then carried out using the two primers. Primers can be selected to amplify the entire regions encoding a full-length DNA or to amplify smaller DNA segments as desired.

The term "preservative", as used herein, is intended to designate a substance showing antimicrobial properties, in particular bactericidal properties and preferably also antifungal properties.

The term "preservative solution," means a solution which comprises preservatives as defined above and other compounds which remove inhibitors of PCR.

The term "sealable" refers to the characteristic of being capable of becoming sealed, i.e., closed with a fastening that must be broken to gain access.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., MOLECULAR CLONING: A LABORATORY MANUAL (2ND ED.), VOLS. 1-3, Cold Spring Harbor Laboratory, (1989) ("Sambrook") or CURRENT PROTOCOLS IN MOLECULAR BIOLOGY, F. Ausubel et al., ed. Greene Publishing and Wiley-Interscience, New York (1987) ("Ausubel").

The phrase "diagnostic analysis" refers to assaying for an analyte typically found in serum. However, for purposes of this invention, the sample preferably is not serum. "Analyte" refers to any compound to be assayed immunologically. Thus it encompasses antibodies, lipids, carbohydrates, drugs and drug metabolites.

The term "diagnostic marker" refers to an analyte, e.g., antibodies, serum proteins, cholesterol, polysaccharides, drugs and drug metabolites, found in bodily fluids such as blood, saliva, vaginal fluid, semen, etc. which allows for the detection of certain physiological conditions, e.g., infection, heart disease, diabetes, autoimmune disease, drug abuse, etc.

The term "diagnostic marker releasing solution (DMRS)" refers to a buffer which is used to extract the protein and extracellular components from the oral fluid in the collection pad. The solutions can be chosen to avoid denaturation or other degradation of the proteins or antibodies, yet release any protein bound to the pad. The solutions are also chosen to prevent cell lysis and contamination of the protein releasing solution with cellular components.

The phrases "TDO" and therapeutic drug oral sample" refers to a biological fluid that is to be assayed for the presence of a therapeutic drug and/or its metabolites. Such drugs include, but are not limited to, theophylline, amphetamines, barbiturates, benzodiazepine, cotinine, proxyphene, carbamazepine, digitoxin, dilantin, phenobarbital, phenytoin, quinidine, teicoplanin, and valproic acid.

DETAILED DESCRIPTION OF THE INVENTION

In this invention, we have developed a method for differentially extracting extracellular analytes from a biological sample to be used in genomic analysis. The sample contains both diagnostic markers and cellular components which contain the genomic markers to be assayed. After collection of the sample, the collection pad is impregnated with a solution that contains a non-ionic detergent and optionally a preservative which selectively extracts the extracellular analytes from the pad yet leaves the cellular components within the pad.

In another embodiment, we have developed a method for the simultaneous collection of genomic and diagnostic markers in biological samples on a single bibulous pad. The diagnostic markers are differentially extracted from the pad by a solution containing a non-ionic detergent which does not lyse the cells containing the genomic markers. The genomic markers are then extracted from the pad by a solution containing a strong detergent and Proteinase K. We have found that this method provides genomic markers that are very stable and can be amplified by PCR and detected by hybridization techniques.

This invention can be utilized to identify diagnostic and genomic marker pairs such as: (1) antibodies directed against HIV and CKR5 Δ32 mutations in the genome; (2) prostate specific antigen and hereditary prostate cancer gene; (3) cotinine and lung susceptibility gene; (4) carcinoembryonic antigen and colon cancer susceptibility genes; (5) serum tumor antigens and the p53 gene; and (6) antibodies directed against HIV and nucleic acid sequences identified as originating from HIV; (7) lipoprotein phospholipase A2 and mutations leading to elevated serum levels; (8) galactokinase and mutations resulting in elevated serum levels; and (9) cathepsin K and mutations leading to elevated serum levels.

A. Biological Fluids to be Sampled

The biological samples to be collected include any samples that contain both cells and extracellular analytes, preferably antibodies, and include vaginal, rectal, nasal, lymph, blood and preferably oral samples, most preferably mucosal transudate.

Vaginal, rectal and nasal collections can be obtained by swabbing the associated tissue by techniques well known in the medical arts. Blood can be collected through venipuncture or by lancing. Lymph can be collected by removal or draining of lymph nodes. Oral samples can be collected by aspiration, expectoration, oral rinses, washes or preferably by absorption into a bibulous pad.

B. Sample Collection

The biological samples can be collected by any of a number of means well known to those of skill in the art. Such means include, but are not limited to venipuncture, aspiration, expectoration, mouth washes or rinses, absorbent sponges, swabs or pads, and so forth.

1. Collection Pads

The preferred sample collection devices are capable of concentrating (preferentially collecting) biological components bearing non-nucleic acid analytes. "Non-nucleic acid analytes" refers to diagnostic markers including drugs, drug metabolites, cholesterol, triglycerides, carbohydrates and proteins such as antibodies. In a particularly preferred embodiment, oral fluids are collected. Indeed, a number of devices, fabricated expressly for sampling oral fluids, are commercially available (e.g. ORAQUICK® and ORASURE® Oral Collection Devices, EPISCREEN™ Oral Collection Devices by Epitope, Inc., RESOLVE® Oral Collection Device by Osborn Labs, OMNISAL® Saliva Collection System by Saliva Diagnostic Systems, Vancouver Wash., USA, etc.). See, also U.S. Pat. Nos. 5,022,409, 5,339,829, 5,335,673, 5,022,409, 5,112,758, 5,234,001, and 5,103,836.

In general, the collection pad can be made of any of a number of absorbent materials suitable for oral use. Preferably, the pad is a thick, absorbent cotton roll or paper, such as commonly used in dental procedures. An example of such a pad is a 1.5 inch No. 2 medium cotton roll distributed by Patterson Dental Co. (Minneapolis, Minn.). Materials such as cellulose, polyurethane, polyester, and rayon are also useful.

In a preferred embodiment, oral samples are collected using such a preferential collection device. The oral fluid produces an average IgG concentration of at least about 1 µg/mL and more preferably at least about 2 µg/mL. In a particularly preferred embodiment, the oral fluid is concentrated to an average of about 8 µg/mL IgG.

Drugs and drug metabolites are typically more dilute in oral fluid. In another preferred embodiment, the collection device produces an average drug (or metabolite) concentration of greater than about 10 ng/mL, most preferably greater than 1 ng/mL.

Typically, the oral sample specimen is collected according to the instructions provided for, or with the particular collection means or device used. The collection pad is held against the gum and cheek until the pad absorbs oral fluid enriched for non-nucleic acid analytes. Typically this involves contact with the gum and cheek for about 2 minutes. The contact can be maintained up to about 5 minutes.

In a particularly preferred embodiment, oral fluid samples are collected with an oral fluid collection device such as the ORASURE® oral fluid collection device (Epitope, Inc., Beaverton, Oreg.). This device comprises an absorbent pad (e.g., cotton or a sponge) affixed to the end of a plunger (e.g., a "syringe" plunger) which acts as a handle. The collection pad of the collector is placed in the mouth of the subject until the collection pad is loaded with oral fluid; typically about four minutes. Alternatively, the EPISCREEN™ Oral Collection Device is used. This device comprises a bibulous pad on a solid support. To extract the oral fluid from the bibulous pad, the pad is inserted into a tube and centrifuged.

2. Hypertonic Solutions

In one embodiment of the invention, the pad is impregnated with one or more salts such that a hypertonic solution forms around the pad during use, thereby enhancing the recovery of the analytes. The salts are provided in an amount effective to recover higher than anticipated concentrations of analytes in the oral fluid. For example, as detailed in U.S. Pat. No. 5,103,836, it is possible to gain an increase in immunoglobulin concentration of as much as 8-16 times when compared to the use of distilled water.

A hypertonic solution is a salt solution which has an ionic strength exceeding that found in blood. In general, salts used in the preparation of the hypertonic solution of the present invention are present in an amount of about 3% or from about 1-20 mg/cm$^2$ dry pad surface.

Salts which can be used in the preparation of the hypertonic solution include alkali metal compounds as well as alkaline earth metal compounds. Preferred salts include sodium chloride, potassium chloride, magnesium sulfate, magnesium chloride and calcium chloride. Sodium chloride is found to be the least toxic, least expensive and most palatable.

The hypertonic solution of the present invention can also include a compound or ingredient for stimulating salivation. The compounds capable of stimulating salivation are found to exhibit a sour taste. These compounds include weak organic acids. Preferred among the weak organic acids are citric acid, ascorbic acid and acetic acid. It is preferred to use citric acid and ascorbic acid at a concentration of between about 0.05% and 0.5% by weight. The preferable-range for acetic acid is between about 0.5% and 3.0% by weight. To provide buffering capacity, the salts of the weak organic acids can be used. The desired pH of the hypertonic solution is from pH 6.0 to 8.5 with 7.0 being preferable. Other types of buffers can be used to provide buffering capacity, such as carbonate or phosphate buffer salts.

In order to minimize degradation in a collected specimen, the absorbent pad or sponge can include a preservative. Such a preservative can act to inhibit proteolytic enzymatic activity which can be responsible for the destruction of nucleic acids, antibodies and other analytes. Compounds contemplated as a preservative include anti-bacterial agents, anti-fungal agents, bacteriostatic agents, fungistatic agents, and enzyme inhibitors. Some of the chemicals contemplated as preservatives include: 0.01-0.1% chlorhexidine digluconate; 0.05-0.5% sodium benzoate; 0.05-0.5% potassium sorbate; antibiotics, such as the sulfate salts of gentamicin, chromamphenicol and streptomycin; protease inhibitors; and phenolic compounds. In one preferred embodiment benzoate, sorbate or the acids thereof are used as antifungal and bacteriostatic agents. Other preferred preservatives are those typically used in medicines and mouthwashes. Examples include ethyl alcohol and chlorhexidine gluconate. Another class of preferred anti-microbial and anti-viral agents are detergents which can be used as topical germicides or in mouthwashes. An example is benzalkonium chloride. It is preferred to use these preservatives in a range of about 0.01% to about 0.2% by weight.

Most materials from which the pad can be made non-specifically bind protein. Thus, it is desired to block proteins from binding to the pad by adding a blocking agent to the hypertonic solution. A blocking agent is generally a soluble protein which is used to prevent non-specific binding of another protein to a solid surface. Compounds which can be added as blocking agents include albumin, gelatin and casein, but any water soluble, non-toxic protein can be used as a blocking agent as long as the protein does not adversely affect the assay being used to assay the analyte or nucleic acid. It is preferred to use bovine gelatin. In general, blocking agents can be added to the hypertonic solution used to impregnate the pad to form a hydrated concentration of between about 0.01% and 0.2% by weight.

In addition to proteinaceous blocking agents, non-ionic detergents, preferably TWEEN-20®, can be used to eliminate non-specific binding of proteins to solid supports. In general, non-ionic detergents can be added to the hypertonic solution to form a concentration in the hydrated pad of 0.05-0.5%. The contents of the hypertonic solution are then incorporated into the pad as described above. One preferred solution is described in U.S. Pat. No. 5,339,829.

The pad is impregnated with the salt(s), weak organic acids, preservatives and blocking agents by known means. A hypertonic solution can be applied to the pad by dipping or spraying the pad so that the components of the solution can be absorbed into and onto the pad which is then allowed to dry. Typically, the pad is dipped into a hypertonic solution and about 1 mL of solution is absorbed. Alternatively, a hypertonic solution could be sprayed onto the pad until a sufficient amount, preferably about 1 mL is absorbed. Excess liquid is shaken off and the pad is placed in a forced-air, convection drying oven at 50° C. for 2 hours or, alternatively, in an oven at 80° C. for 6-12 hours in the absence of forced air.

C. Diagnostic Marker Releasing Solutions

The collection pad, containing oral fluid, can be impregnated with diagnostic marker releasing solutions (DMRS) to differentially extract the extracellular analytes from the cellular components in the pad. The incubation of the pad and the DMRS can take place within the collection device or in a separate tube. The volume of DMRS can range from 0.5-2.0 mL, preferably 0.75 -1.0 mL presuming a pad capable of absorbing approximately 1 mL of oral sample. DMRS comprises a detergent that will not lyse cells at low concentrations, e.g., TWEEN-20®, TRITON X-100® and NONIDET P-40®. The preferred detergent is TWEEN-20®. The concentration of detergent can range from 0.02-1% but is preferably 0.5%. This concentration gives a final concentration in the mixture of DMRS and oral fluid of about 0.2%. In addition to a gentle detergent, DMRS may also comprise a preservative, e.g., 0.05-0.5% chlorhexidine digluconate, 0.05-0.5% sodium benzoate, 0.05-0.5% potassium sorbate, 0.001-0.2% sodium azide, 0.001-0.2% mercury containing salts, such as thimerosal and phenylmercuric salts, antibiotics, such as the sulfate salts of gentamicin, chromamphenicol and streptomycin, protease inhibitors, and phenolic compounds.

Optionally, DMS may comprise salts and buffering compounds. Salts which can be used in the preparation of the DMRS include alkali metal compounds as well as alkaline earth metal compounds. Preferred salts include sodium chloride, potassium chloride, magnesium sulfate, magnesium chloride and calcium chloride. The salts which can be used in the DMRS should be present in a concentration of about 1-3%.

The DMRS of the present invention can also include a buffering compound. These compounds typically include the salts of weak organic acids. Preferred among the weak organic acids are citric acid, ascorbic acid and acetic acid. It is preferred to use citric acid and ascorbic acid at a concentration of between about 0.025% and 0.25% by weight. The preferable-range for acetic acid is between about 0.25% and 1.5% by weight. The desired pH of the DMRS can be from pH 6.0 to 8.5 with 7.0 being preferable. Other types of buffers can be used to provide buffering capacity, such as carbonate or phosphate buffer salts.

Incubation of the collection pad in DMRS can be at temperatures ranging from 4°-37° C., preferably 20°-25° C. The length of incubation can be from 30 min to 72 hours, depending on the convenience of the operator. After incubation, the pad contents, including the extracellular analytes of the oral sample and DMRS, are physically extracted from the pad and can be tested immediately or placed in a container for transport to a testing site. The oral fluid-DMRS may be left "untreated" during storage and transport. Alternatively, the oral fluid-DMRS can be combined with various "storage" solutions that may act as diluents, buffers, preservatives, and the like. The oral fluid-DMRS alone, or in combination with the storage solution, can be desiccated or frozen for transport according to means well known to those of skill in the art.

To express the oral sample with the DMRS, the collection pad in the sample collection device can be compressed, by depression of the plunger, until the fluid coming out of the collection device adequately fills the sample well of the assay device, or other collection receptacle. Detailed descriptions of such collection devices can be found in U.S. Pat. Nos. 5,339,829 and 5,479,937. Alternatively, the oral fluid and DMRS in the pad can be collected by aspirating the contents of the pad under vacuum or by centrifugation of the pad and the collection of the oral fluid into a collection tube (as with the EpiScreen® Oral Collection Device).

D. Assay Diluents

After the oral fluid-DMRS sample has been expressed from a collection device into a storage device, an assay diluent can be added to dilute the analyte and optimize the sample. The diluent chosen will depend in most part on the assay to be performed.

Assay diluents are chosen so they will not interfere with the binding of analytes in the subject assay. Because the analytes are typically determined by immunoassay, the assay diluents are usually chosen to avoid denaturation or other degradation of proteins or antibodies and to provide a milieu compatible with and facilitating of antibody/target (epitope) binding. While any assay diluent typically used in immunoassays is suitable (See, e.g., CURRENT PROTOCOLS IN IMMUNOLOGY Wiley/Greene, N.Y.; Harlow and Lane (1989); ANTIBODIES: A LABORATORY MANUAL, Cold Spring Harbor Press, N.Y.; Stites et al. (eds.) BASIC AND CLINICAL IMMUNOLOGY (4TH ED.) Lange Medical Publications, Los Altos, Calif., and references cited therein), preferred assay diluents range from about pH 7 to about pH 9, more preferably from about pH 7.5 to about pH 8.5, and most preferably around pH 8. Any buffer salt with a buffering capacity in that range can be used, e.g., Tris, tricine, phosphate, borate and carbonate, a particularly preferred assay diluent comprises $NaHCO_3$. The concentration of buffer salts can range from 0.01 to 0.3 M, preferably, 0.1 to 0.15 M. One of the preservatives in the DMRS can also be added at a concentration of about 0.01-0.2%, preferably about 0.01%.

One of skill in the art will appreciate that the assay diluent can additionally include a protein or other moiety, unrelated to the target antibody, which participates in non-specific binding reactions with the various components of the assay (e.g., the substrate) and thereby blocks and prevents non-specific binding of antibodies in an immunoassay. A particularly preferred blocking agent is bovine serum albumin (BSA) or polyvinyl alcohol (PVA).

In one embodiment, the oral fluid-DMRS sample is diluted at an assay diluent:sample ratio ranging from about 1:1 up to about 1:20 (v/v), more preferably from about 1:1 up to about 1:15 (v/v) and most preferably from about 1:1 up to about 1:10 (v/v). In one particular preferred embodiment, the oral fluid-DMRS sample is diluted at an assay diluent:sample ratio of about 1:8 (v/v). In certain embodiments, the oral fluid-DMRS sample may not be diluted at all prior to use.

After the sample has been removed from the pad, assays to detect the analyte of interest can be performed. Such assays include, but are not limited to fluid or gel precipitin reactions, agglutination assays, immunodiffusion (single or double), immunoelectrophoresis, immunosorbent assays, various solid phase assays, immunochromatography (e.g., lateral flow immunochromatography) and more preferably radioimmunoassay, enzymatic immunoassay and most preferably ELISA. Methods of performing such assays are well known to those of skill in the art (see, e.g., U.S. Pat. Nos. 4,366,241; 4,376,110; 4,517,288; 4,837,168; 5,405,784; 5,534,441; 5,500,187; 5,489,537; 5,413,913; 5,209,904; 5,188,968; 4,921,787; and 5,120,643; British Patent GB 2204398A; European patent EP 0323605 B1; METHODS IN CELL BIOLOGY VOLUME 37: ANTIBODIES IN CELL BIOLOGY, Asai, ed. Academic Press, Inc. New York (1993); AND BASIC AND CLINICAL IMMUNOLOGY 7TH EDITION, Stites & Terr, eds. (1991)). All of which are herein incorporated by reference.

E. Nucleic Acid Releasing Solutions

To detect nucleic acid from the biological sample, the pad from which the oral sample and DMRS was extracted can be impregnated with a nucleic acid releasing solution (NARS). The nucleic acids extracted from the pad are concentrated, preferably by precipitation, and electrophoresed in agarose gel to determine the quantity of genomic DNA extracted from the pad.

To determine whether a specific DNA sequence is present in the genomic DNA eluted from the pad, a desired portion of the DNA eluted from the pad is amplified by PCR techniques, using sequence specific primers, and then visualized by agarose gel electrophoresis or by hybridization techniques if necessary.

1. Extraction of Nucleic Acids

After the physical extraction of most of the extracellular analytes of the sample in PRS, the pad containing the cellular components is impregnated with nucleic acid releasing solution (NARS). The NARS chosen should act to stabilize nucleic acids and optimize extraction of nucleic acids from the absorbent pads. Preferred NARS comprise low concentrations (e.g., 0.01-0.1 M) of buffer salts with a buffering capacity of about pH 6 to pH 9, such as Tris, phosphate, borate, HEPES, tricine, etc. Such solutions may also comprise chelating or other agents which inhibit nucleases. Preferred chelating agents are EDTA, EGTA, sodium tripolyphosphate, and ethylenediaminetetra-(methylenephosphonic acid) (EDTPO). The concentration of the chelating agent can range from 0.01-0.3 M, preferably 0.1-0.2 M. A strong detergent or another compound useful for lysing whole cells can be added, for example SDS, hexadecyltrimethylammonium bromide (CTAB), guanidine hydrochloride, guanidinium thiocyanate and organic solvents such as phenol. Concentrations of cell lysing compounds will vary depending on the agent used. In addition, the NARS can contain a proteinase, such as Proteinase K, or some other compound capable of degrading proteins under the conditions provided by the NARS. These compounds would include some of those used to disrupt cellular membranes and lyse whole cells, for example, SDS, guanidine hydrochloride and phenol. Again, the concentrations of these compounds will depend on the protein denaturation strength of the compounds. A preferred NARS is composed of 0.01 M Tris-HCl, 0.1 M EDTA, pH 8.0, 0.5% SDS and 100 µg/mL Proteinase K.

After absorption of most of the NARS, the pad and the remaining NARS are centrifuged to recover the NARS containing the genomic marker. In a preferred embodiment, the collection pad is placed in a centrifuge tube, a hole made in the bottom of the tube and the tube inserted into another centrifuge tube. The two tubes are centrifuged at low speeds, piggy-back style.

Those skilled in the art will recognize other methods of extracting fluids from fluid collection devices, such as incubation at elevated temperatures and physical means, e.g., sonication, mincing of the pad and elution into a nucleic acid extraction buffer and shearing of the cells containing the nucleic acids from the pad.

2. Concentration and Purification of Nucleic Acids

After the genomic marker has been extracted from the pad, the nucleic acids are optionally isolated and in a preferred embodiment, concentrated for use in genomic analysis. One of skill in the art will recognize that there are many methods employed to separate nucleic acids from other cellular components. For example, to the extracted genomic DNA, an equal volume of 3-6 M, preferably 6 M NaCl or ammonium acetate can be added. Alternatively, the nucleic acids can be analyzed without isolation or concentration.

In another embodiment, the extracted genomic DNA is incubated with 1 volume of ProCipitate reagent (a water insoluble anion exchanger which binds proteins, CPG, Inc.) for 5 min. at room temperature and centrifuged in a microcentrifuge at the full speed for 5 min. The DNA in the supernatant is precipitated according to the techniques described below. In yet another embodiment, the extracted genomic DNA is mixed by inverting the sample rapidly with a 25:25:1 mixture of phenol:chloroform:isoamyl alcohol. After a quick centrifugation to separate the phenolic and aqueous phases, the aqueous phase is drawn off to a clean microcentrifuge tube and extracted with 1 volume of 50:1 chloroform: isoamyl alcohol. The DNA in the aqueous phase is precipitated as described below.

In a preferred embodiment, to 1 volume of the extracted genomic DNA is added ⅓ volume of 10 M ammonium acetate. The mixture is mixed and chilled for 10-15 minutes. After centrifugation, the DNA contained in the supernatant is precipitated as described below.

To concentrate the genomic DNA, typically precipitation methods are utilized. In a preferred embodiment, 2 volumes of 100% ethanol is added to the nucleic acid solution and the nucleic acid/ethanol solution is incubated overnight at −70° C. Those skilled in the art will recognize that there are other methods of precipitating nucleic acids with alcohol. These include but are not limited to incubation with isopropanol, incubation at a final concentration of 75% ethanol, isopropanol, etc.

Centrifugation of the ethanol precipitated DNA concentrates the DNA. The DNA is then washed, preferably with 75% ethanol, and dried, preferably air-dried. One of skill in the art will recognize that drying nucleic acids can be accomplished in a variety of ways, including but not limited to drying in a fume hood, in a centrifuge to which a vacuum has been applied, etc. One of skill in the art will also recognize that there are other ways of concentrating nucleic acids, such as forced filtration by centrifugation, specific binding to hydroxylapatite coated membranes with consequent elution, etc.

Once the precipitated nucleic acid has dried, it can resuspended in a small volume of 10 mM Tris-HCl, pH 8.0, 0.1 M EDTA (TE) and stored until agarose gel electrophoresis is performed. Storage can be from 4° C. to -70° C. One of skill in the art will recognize the colder the storage temperature the longer the nucleic acid can be stored.

3. Agarose Gel Electrophoresis of Genomic Nucleic Acids

Before specific nucleic acid sequences are amplified to determine their presence in the genomic DNA, it may be useful to determine the presence and quantity of genomic DNA. One of skill in the art will recognize there are many standard methods to quantitate DNA, including but not limited to, $A_{260}/A_{280}$ measurement, colorimetric assays, dipstick blot assays, fluorescence determination with a fluorophore which preferentially binds to nucleic acids, for example Hoechst H33258 dye (DyNA Quant 200 fluorimeter, Pharmacia) etc. A preferred method is to electrophorese a portion of the nucleic acid sample in an agarose gel and visualize the nucleic acids by ethidium bromide staining.

The agarose gel should be prepared according to standard techniques. See, Sambrook, et al. (1989) or Ausubel et al., eds., CURRENT PROTOCOLS IN MOLECULAR BIOLOGY, Greene Publishing and Wiley-Interscience, New York (1987), both of which are incorporated herein by reference. Typically, to measure genomic DNA, the concentration of agarose in the gel should be quite low; 0.5%. The agarose is melted in electrophoresis buffer containing 0.5 µg/mL ethidium bromide and poured on the gel platform. After cooling to room temperature, the gel is submerged in electrophoresis buffer in the gel chamber. Typically, electrophoresis buffer contains 0.01 M Tris-HCl, 0.1 mM sodium acetate, 1 mM EDTA, pH 7-8 (TAE).

The nucleic acid samples are electrophoresed towards the cathode at 25-100 volts, more preferably at 50 volts for a sufficient length of time for nucleic acids to penetrate the agarose gel. The nucleic acids can be visualized as an orange band under ultraviolet (UV) light. The intensity of the orange sample band is compared to the intensity of bands of known amounts of DNA. A rough quantitation of sample DNA concentration can thus be obtained.

4. Amplification of Nucleic Acid of Interest

In addition to the PCR techniques described below, one of skill will recognize other methods can be used to amplify nucleic acid sequences such as ligase chain reaction (LCR) (see Wu and Wallace, Genomics, 4: 560 (1989); Landegren et al., Science, 241:1077 (1988) ("Landegren"); and Barringer et al., Gene, 89:117 (1990) ("Barringer"); transcription amplification (Kwoh et al., Proc. Natl. Acad. Sci. USA, 86:1173 (1989) ("Kwoh")); and self-sustained sequence replication (Guatelli, et al., Proc. Nat. Acad. Sci. USA, 87:1874 (1990) ("Guatelli")).

PCR techniques are well described in the literature, see, for example, Sambrook and Ausubel, and one of skill in the art will recognize that PCR procedures can be changed depending on, but not limited to, the length of the sequence to be amplified, the size of the primers, and the nucleotide content of the amplified sequence.

To amplify a specific nucleic acid sequence of genomic DNA, 3' and 5' primers of between 5-10 nucleic acids that flank the desired sequence are synthesized. This can be done synthetically through methods well known in the molecular biology art.

To a PCR tube is added, individual nucleotides, 3' and 5' primers flanking the region desired to be amplified, Taq polymerase, the nucleic acid sample and the necessary buffers and salts. High quality mineral oil or some other solution useful to prevent evaporation is applied to the top of the solution.

The tube (along with controls) is incubated in a thermocycler that heats the sample to 95° C. to denature the double stranded nucleic acid, then drops the temperature to 55° C. to allow for annealing of the primers to the single stranded nucleic acid and then heats the sample to 72° C. for polymerization of the double stranded sequence. This process is repeated by the thermocycler for a predetermined length of time. One of skill in the art will appreciate that the temperatures used, and the length of time of the cycles depend on the nature of the nucleic acid sequence to be amplified.

5. Agarose Gel Electrophoresis of PCR Products

Because the amplified sequences are smaller in size than the genomic DNA of step (3), the gel should be of higher agarose concentration. One of skill in the art will recognize the agarose concentration of the gel depends on the size of the amplified sequence to be identified.

PCR-amplified sequences may be directly visualized from the ethidium bromide stained sequence in the agarose gel. If a band of the expected size is clearly visible, the presence of the desired sequence is determined and a positive result obtained. However, there may not be enough material to see the amplified material. If a band is not detectable by ultraviolet light, the amplified sequence is transferred to a membrane and probed with a labeled nucleic acid sequence. Labels can include radioisotopes, chemiluminescent dyes, biotin and in a few circumstances, enzymes.

Southern blotting techniques are well known to those of skill in the art. Briefly, the contents of the agarose gel are transferred, either through capillary action or electrophoresis to a membrane (nylon or nitrocellulose are two exemplary membranes). The nucleic acids are hybridized to the membranes (via ultraviolet light for nylon membranes and heat for nitrocellulose) and then incubated in hybridization buffer. Hybridization buffer typically comprises from about 20 to 60% volume, preferably 30%, of a polar organic solvent. A common hybridization solution employs about 30-50% v/v formamide, about 0.15 to 1 M sodium chloride, about 0.05 to 0.1 M buffers, such as sodium citrate, Tris-HCl, PIPES or HEPES (pH range about 6-9), about 0.05 to 0.2% detergent, such as sodium dodecyl sulfate, or between 0.5-20 mM EDTA, FICOLL® (Pharmacia Inc.) (about 300-500 kD), polyvinylpyrrolidone (about 250-500 kD), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or hydrating agents, such as polyethylene glycol, anionic polymers such as polyacrylate or polymethylacrylate, and anionic saccharidic polymers, such as dextran sulfate.

Next, the soluble labeled probe of about 18-25 nucleotides complementary to the amplified sequence is hybridized to the amplified sequence, forming a hybridization duplex with the immobilized nucleic acid probe on the solid support. The presence of the amplified sequence is then determined in accordance with the label being used. A general reference for various detection methods can be found in Hames, B. D. and Higgins, S. J., NUCLEIC ACID HYBRIDIZATION, IRL Press, Oxford, 1985 ("Hames and Higgins").

Hybridization techniques are generally described in Hames and Higgins; Gall and Pardue (1969) Proc. Natl. Acad. Sci., USA, 63: 378-383, and John, Burnsteil and Jones (1969) Nature 223: 582-587. As improvements are made in hybridization techniques, they can readily be applied.

F. Systems and Kits for the Collection of Both Genomic and Diagnostic Information from a Single Sample.

The invention provides for a system for removing deleterious extracellular analytes from an oral sample destined for use in genomic analysis. Deleterious extracellular analytes are compounds that would interfere with such genomic analysis. The oral sample comprises both cellular components and extracellular analytes. The system comprises the collection of the oral sample on the bibulous pad and impregnation of the pad with a solution comprising a non-ionic detergent which can selectively extract the extracellular analytes from the pad and allow the cellular components to remain within the pad.

In another embodiment, the system comprises of preparing an oral sample for both genomic and diagnostic analysis. In this embodiment of the invention, the diagnostic analysis is done on the extracellular analytes extracted from the bibulous pad.

The instant invention also provides for kits to rapidly and conveniently collect and detect both diagnostic and genomic information from a single sample. An exemplary kit comprises the biological fluid collection device containing a bibulous solid support with or without impregnation with the hypertonic solution capable of extracting the diagnostic markers from the solid support, the diagnostic marker releasing buffer solution and buffers necessary for extracting the genomic marker by lysing whole cells retained on the solid support. If the kit was directed to a preferred pair of genomic and diagnostic markers, the kit could also contain antibodies to the analyte of interest and primers and probes to the genomic marker of interest. In addition to reagents, the kit would also contain instructions for use.

In the case of a kit to be used for the collection of a drug of abuse, e.g., cocaine, methamphetamine, etc., it is necessary to seal the containers holding the extracted samples prior to assay. In this embodiment, the kit also contains means for holding the extracts from the bibulous pad, e.g., centrifuge tubes. Optimally, the tubes are capable of being sealed, i.e., closed with a fastener that must be broken to open the tube. Preferably, the kit would contain a labeling means for identifying the source of the sample. The labeling means is attachable to the support for the bibulous pad, as well as the means for holding the extracted solutions. The labeling means need not name the source, and in fact, preferably does not, but identifies the source by number or most preferably by a bar code.

E. EXAMPLES

Example 1

Detection Of DNA from ORASURE® Pad

An ORASURE® pad was placed in the mouth of a human for four minutes. The pad was placed in the accompanying vial containing preservative and, at some time later, centrifuged at 2500 rpm for 15 minutes according to the manufacturer's instructions. The oral fluid expressed from the pad was stored at 4° C. for later use.

The genomic DNA was extracted from the pad by incubating the pad for 30 minutes at 55° C. in 1.0 mL of nucleic acid releasing solution (10 mM Tris, pH 8.0, 0.1 M EDTA and 0.5% SDS; all from BioWhittaker, Mass.) to which was added 100 μg Proteinase K (5'-3', Inc., CO). The pad was then placed in the original vial, which was inserted into a 15 mL polypropylene centrifuge tube and centrifuged at 2500 rpm for 15 minutes. The recovery of fluid was approximately 1.0 mL.

To 1.0 mL of pad extract was added 1 mL 6M NaCl. The tube was shaken vigorously for 15 minutes and centrifuged at 2500 rpm for 15 minutes. The supernatant was transferred to a clean tube and 0.8 mL of TE buffer (10 mM Tris-HCl, pH 8.0, 0.1 mM EDTA) was added. Two volumes of 100% ethanol and 10 μL of nucleic acid pellet paint (e.g., Pellet Paint CO-PRECIPITANT®, Novagen) was added. The contents of the tube were centrifuged for 10 minutes to precipitate the DNA. The DNA pellet was washed twice with 75% ethanol by removing the supernatant and resuspending the DNA. After the last centrifugation, the DNA pellet was allowed to air-dry. The dried pellet was resuspended in 20 μL TE buffer and stored at 4° C. overnight.

A 0.5% agarose (LE, Seakem) gel was prepared in 1×TAE and 0.5 μg/mL ethidium bromide. One μL of the DNA solution was added to 9 μL of 10×Electrophoresis sample buffer (0.1 M Tris, pH 8.0, 10 mM EDTA, 0.25% Bromophenol Blue, 0.25% Xylene Cyanol and 1% glycerol). The sample was loaded onto the gel bed and electrophoresed in 1×TAE for two hours at 50V. A faint band of high molecular weight DNA was visible by UV light.

2. Example 2

PCR Amplification of β-globin DNA

Note: all PCR reagents are from Perkin-Elmer. The PCR buffer was prepared as follows: 50 μL of PCR buffer, 10 μL 25 mM MgCl$_2$, 40 μL dNTP (2.5 mM each),5 μL of 50 μM HBGlob5 (Operon, Ill.) and 5 μL of 50 μM HBGlob3 (Operon, Ill.). These primers will produce an amplified DNA sequence of 200 bp. To 22 μL of PCR buffer was added 10 μL DNA sample from Example 1 and 68 μL H$_2$O for a final volume of 100 μL. Each tube was topped with mineral oil. Before PCR amplification, 5 μL of Taq polymerase was added to the tubes.

The globin sequence was amplified for 28 cycles; with separation of strands at 94° C., annealing of primers at 55° C. and polymerization at 72° C. At the end of the amplification run, the sample was stored at 6° C.

20 μL of amplified DNA was electrophoresed in a 1.0% agarose gel for 20 minutes at 100 V. Upon UV radiation, a strong band appeared at 200 bp, as expected. The amplified nucleic acid was sequenced and found to agree exactly with the expected sequence.

3. Example 3

Determination of the Optimal DNA Extraction Method

Samples were collected using two ORASURE® devices (from a single subject), the genomic DNA extracted from each pad was divided into 4 equal volumes (350 μL each), and processed separately using the NaCl, ProCipitate, phenol extraction and the ammonium acetate methods. The quantity of DNA extracted is listed in Table 1. Since the ammonium acetate method proved to be the most efficient, two additional pads and additional cotton swabs were processed to confirm the method. The results are included at the bottom of Table 1.

Figure 2:
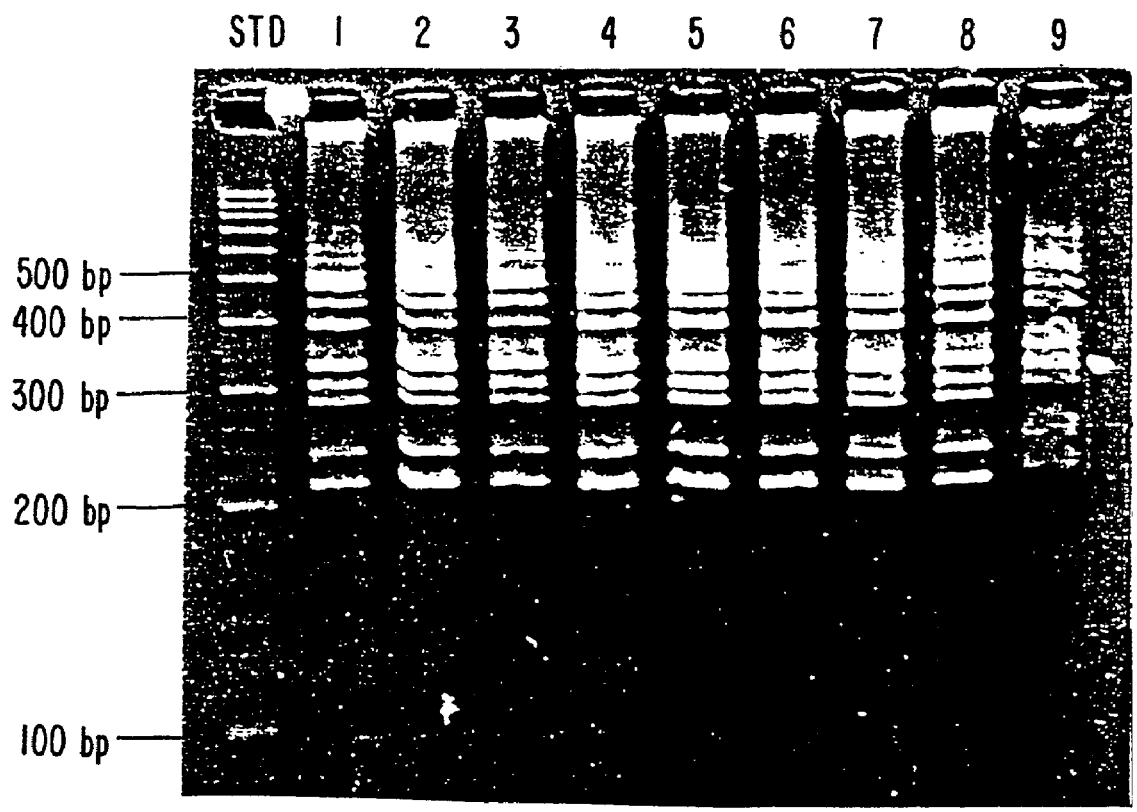
FIG. 2 is a photographic image of an agarose gel of PCR products using various DNA concentration methods. Lane "Std" contains the 100 bp ladder standard, lane 1 contains DNA purified using the phenol-chloroform method, lane 2: sodium chloride method, lane 3: ProCipitate method, lanes 4-8, various preparations using the ammonium acetate method. The lane numbers correspond to row numbers in Table 1. Lanes 5 and 6, DNA purified from ORASURE® pads, lanes 7 and 8, DNA purified from cotton swabs. Lane 9 contains PCR products from a standard human DNA preparation. The concentrations of DNA are listed in Table 1.

The quality of the various DNA samples were analyzed using PCR. Multiplex PCR was utilized because of the complexity of the CFTR gene and the requirement for DNA of high quality. In the test, the 9 exons of the CFTR gene were multiplexed in a single tube (see below for CFTR PCR protocol). The results of the exon amplification experiment using multiplex PCR are displayed in FIG. 2. The quality of all the DNA sample preparations was acceptable.

TABLE 1

Comparison of Extraction Methods

| Sample No. | DNA Extraction Method | DNA (μg/mL) | Total Volume (mL) | DNA/2 Pad | Total DNA/pad |
|---|---|---|---|---|---|
| 1 | Phenol-chloroform | 47 | 0.04 | 1.88 | 3.78 |
| 2 | Sodium chloride | 26 | 0.08 | 2.08 | 4.16 |
| 3 | ProCipitate | 42 | 0.04 | 1.68 | 3.36 |
| 4 | Ammonium acetate | 51 | 0.04 | 2.04 | 4.08 |

DNA Extraction by Ammonium Acetate

| Device | DNA (μg/mL) | Total Vol. (mL) | DNA/1/2 device (μg) | DNA/device (μg) | Average DNA/device (μg) |
|---|---|---|---|---|---|
| 5 Orasure | 30 | 0.04 | 1.2 | 2.4 | Orasure: 2.48 |
| 6 Orasure | 32 | 0.04 | 1.28 | 2.56 | |
| 7 Swab | 39 | 0.04 | | 1.56 | Swab: 1.56 |
| 8 Swab | 39 | 0.04 | | 1.56 | |

4. Example 4

Comparison of DNA Extraction with or without Preservatives

To determine whether the protein releasing solution enhanced recovery of nucleic acids from the collection pad, a comparison was made between DNA collected from sample collection pads with or without first impregnating the pads with PRS.

Figure 3:
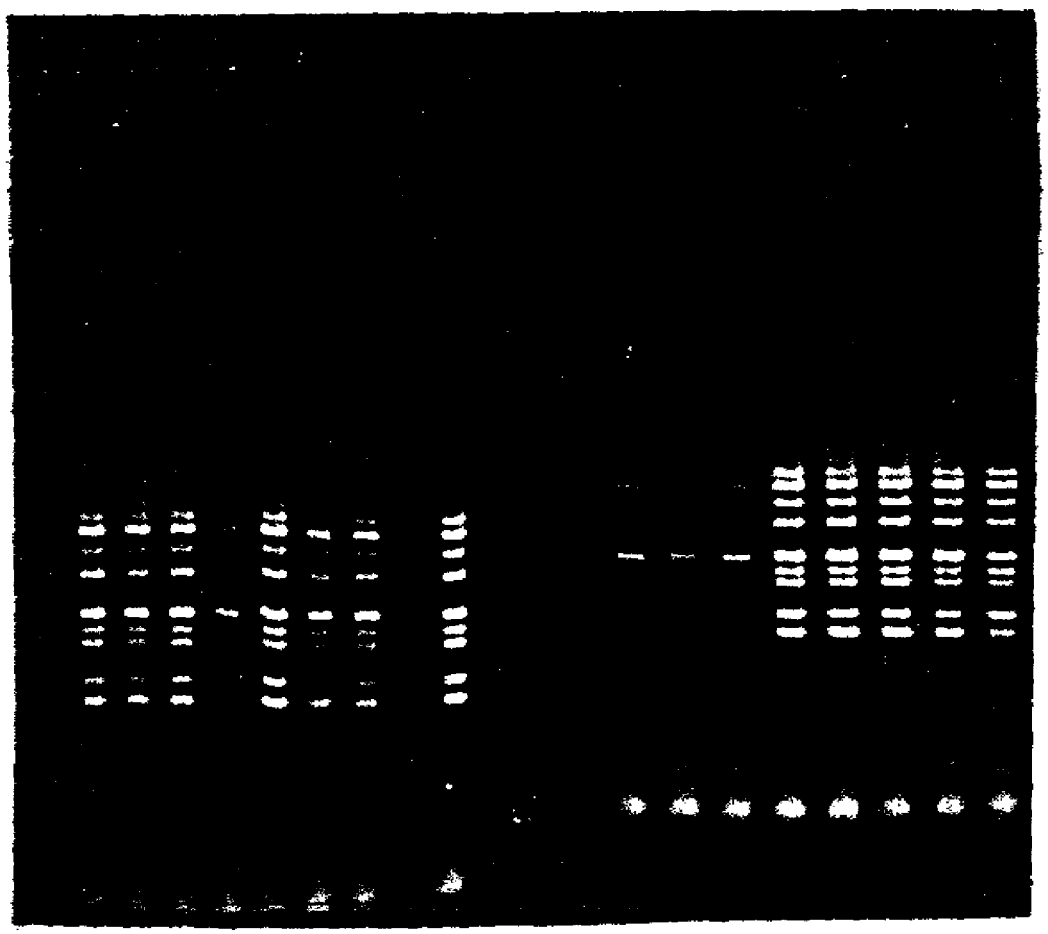
FIG. 3 is a photographic image of an agarose gel showing PCR products amplified from DNA purified by the ammonium acetate method from "wet" (preservative treated) and "dry" ORASURE® pads. Numbers correspond to individual DNA preparations obtained from specific persons listed in Table 2. The numbers in the top row correspond to DNA purified from wet pads, the numbers in the lower row correspond to DNA purified from dry pads.

These results are presented in Table 2 and FIG. 3. There was approximately 30% more DNA recovered from the untreated pad compared to the PRS-treated pads. However, the quality of the DNA was more consistent in the PRS-treated pads. Some of the pads that had not been incubated with PRS were discolored, presumably, the extracellular analytes absorbed by the pad adversely affected the assay. The preservative in the ORASURE® device apparently removes, or otherwise negates the adverse effects of these substances on the PCR reactions in these experiments.

A pellet was also collected from the preservative wash. The pellet, possibly buccal cell material, was small, and yielded negligible amounts of DNA (approximately 10% of the total preparation).

TABLE 2

Effect of the PRS on DNA Extraction

| Sample No. | DNA (µg/mL) | Total Vol. (mL) | DNA/pad (µg) | CF Amplification Results |
|---|---|---|---|---|
| 1 | 71 | 0.04 | 2.84 | Expected banding pattern |
| 2 | 28 | 0.04 | 1.12 | Expected banding pattern |
| 3 | 60 | 0.04 | 2.4 | Expected banding pattern |
| 4 | 43 | 0.04 | 1.72 | Expected banding pattern |
| 5 | 43 | 0.04 | 1.72 | Expected banding pattern |
| 6 | 24 | 0.04 | 0.96 | Weak banding pattern[1] |
| 7 | 29 | 0.04 | 1.16 | Expected banding pattern |
| 8 | 76 | 0.04 | 3.04 | Expected banding pattern |
| Average, wet pads | | | 1.87 | |
| 1 | 90 | 0.04 | 3.6 | Expected banding pattern |
| 2 | 28 | 0.04 | 1.12 | Weak banding pattern |
| 3 | 62 | 0.04 | 2.48 | Expected banding pattern |
| 4 | 96 | 0.04 | 3.84 | Did not work |
| 5 | 14 | 0.04 | 0.56 | Weak banding pattern |
| 6 | 19 | 0.04 | 0.76 | Weak banding pattern |
| 7 | 101 | 0.04 | 4.04 | Expected banding pattern |
| 8 | 89 | 0.04 | 3.56 | Expected banding pattern |
| Average, dry pads | | | 2.495 | |

[1]Weak banding patterns indicate poor quality DNA

5. Example 5

Collection of Genomic DNA by ORASURE® Collection Pads and Multiplex PCR of the CFTR Gene DNA quantities collected from 28 ORASURE® pads are presented in Table 3. DNA was extracted and purified from 28 ORASURE® pads using the ammonium acetate procedure described above. From each purified sample, a 10 µM stock solution of DNA was prepared. From that stock solution, 25 µL aliquots were used for CF exon amplification.

Suitability for the CF multiplex PCR amplification was determined by amplifying 9 exons from the CFTR gene in a single PCR amplification tube. Testing against a positive control, all 9 exons must be present on a 1.5% agarose gel for a positive CFTR result.

Figure 4:
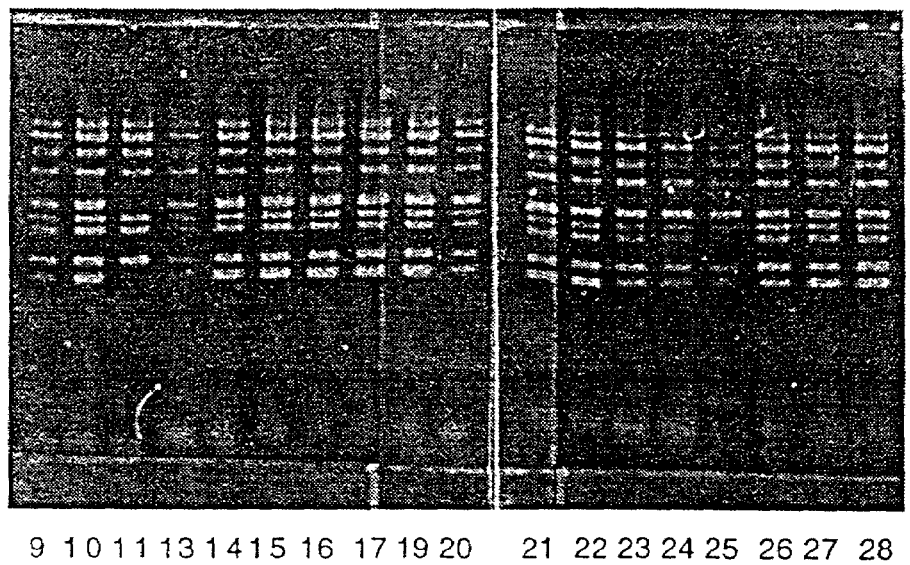
FIG. 4 is a photographic image of an agarose gel of CFTR multiplex PCR products amplified from ORASURE® pads. The protocol is given in Example 5 and in Table 3.

All 18 samples tested by amplifying 9 exons of the CFTR gene produced the expected banding pattern. The gel results are presented in FIG. 4.

TABLE 3

DNA Collected from Orasure Pads for CFTR PCR

| Sample No. | Vial lot # | Pad lot # | DNA (µg/mL) | Total Vol. (mL) | DNA/pad (µg) |
|---|---|---|---|---|---|
| 1 | v159-3 | k166-3 | 71 | 0.04 | 2.84 |
| 2 | v159-3 | k166-3 | 28 | 0.04 | 1.12 |
| 3 | v159-3 | k166-3 | 60 | 0.04 | 2.4 |
| 4 | v159-3 | k166-3 | 43 | 0.04 | 1.72 |
| 5 | v159-3 | k166-3 | 43 | 0.04 | 1.72 |
| 6 | v159-3 | k166-3 | 24 | 0.04 | 0.96 |
| 7 | v159-3 | k166-3 | 29 | 0.04 | 1.16 |
| 8 | v159-3 | k166-3 | 76 | 0.04 | 3.04 |
| 9 | v159-3 | k166-3 | 59 | 0.04 | 2.36 |
| 10 | v159-3 | k166-3 | 30 | 0.04 | 1.2 |
| 11 | v159-3 | k166-3 | 23 | 0.04 | 0.92 |
| 12 | v159-3 | k166-3 | 5 | 0.04 | 0.2 |
| 13 | v159-3 | k166-3 | 28 | 0.04 | 1.12 |
| 14 | v159-3 | k166-3 | 28 | 0.04 | 1.12 |
| 15 | v159-3 | k166-3 | 45 | 0.04 | 1.8 |
| 16 | v159-3 | k166-3 | 55 | 0.04 | 2.2 |
| 17 | v159-3 | k166-3 | 37 | 0.04 | 1.48 |
| 18 | v159-3 | k166-3 | 7 | 0.04 | 0.28 |
| 19 | v159-3 | k166-3 | 97 | 0.04 | 3.88 |
| 20 | v159-3 | k166-3 | 55 | 0.04 | 2.2 |
| 21 | v140-3 | | 42 | 0.04 | 1.68 |
| 22 | v140-3 | | 17 | 0.04 | 0.68 |
| 23 | v140-3 | | 33 | 0.04 | 1.32 |
| 24 | v140-3 | | 35 | 0.04 | 1.4 |
| 25 | v140-3 | | 16 | 0.04 | 0.64 |
| 26 | v140-3 | | 16 | 0.04 | 0.64 |
| 27 | v140-3 | | 36 | 0.04 | 1.44 |
| 28 | v140-3 | | 62 | 0.04 | 2.48 |
| Average | | | 39 | | 1.57 |
| Standard Deviation | | | 20 | | 0.86 |
| Median | | | 37 | | 1.42 |

6. Example 6

Collection of Genomic DNA by ORASURE® Collection Pads and PCR of the Spinocerebellar Ataxia (SCA2) Gene The DNA samples collected in Example 5 were also used for detection of the SCA2 gene by PCR amplification. 2.5 µL aliquots of the DNA samples were used for SCA2 amplification.

Suitability for the SCA2 PCR amplification was determined by amplifying an approximately 130-140 bp fragment of the SCA2 gene containing a variable trinucleotide region. An expansion of this variable region from the wild type configuration (typically 15-25 CAG [glutamine] repeats) to 37 CAG repeats, or more, indicates a high likelihood of current or future Ataxia disease. A suitable SCA2 PCR product band must be sufficiently distinct to determine +/−3 (CAG) trinucleotide repeats, so that wild types can be readily distinguished from disease-associated genes carrying the repeat expansion.

Figure 5:
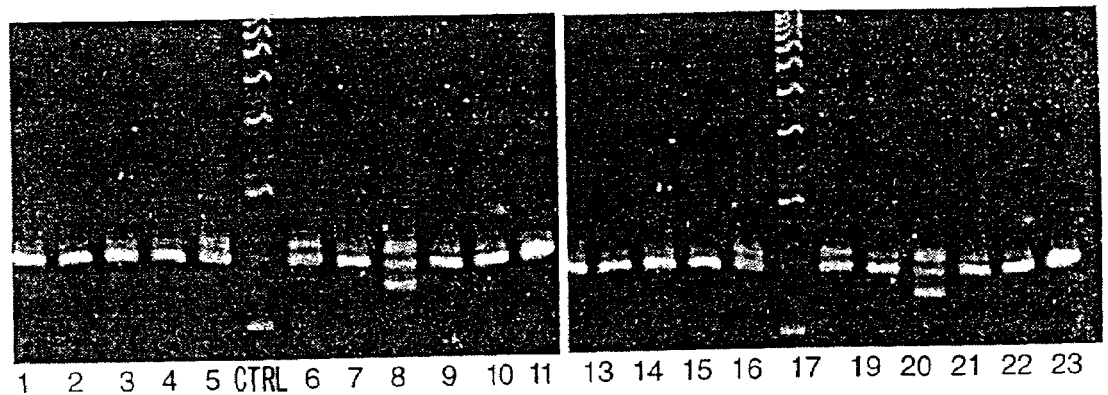
FIG. 5 is a photographic representation of an agarose gel of PCR products from DNA isolated from ORASURE® pads. The samples were amplified with primers specific for the SCA2 gene. Note that individual#8 has an allele shorter than average.

20 samples tested by amplifying the gene fragment bracketing the variable trinucleotide repeat region of the SCA2 gene produced results consistent with wild type gene. All produced amplified PCR product bands in the 130-140 bp with the exception of one heterozygote sample which yielded one 130-140 bp fragment and one 120-130 bp band. None of the samples yielded a product band at the 170 bp range which would be consistent with disease genotype. The band resolution for the SCA2 test was +/−2 trinucleotide repeats. The gel results of the Ataxia amplification are presented in FIG. 5.

7. Example 7

Simultaneous Collection of Antibodies to HIV and DNA Containing the CKR5 Gene ORASURE® pads were used to sample a population of 148 individuals at high risk for HIV infection. By western blot assay on the oral fluid extracted from the pads, 100 of the individuals did not have antibodies to HIV while 48 of the individuals did have antibodies to HIV.

A molecular diagnostic test was designed and performed on the 148 samples in order to determine the presence or absence of mutated forms of the CKR5 HIV infection gene (Human CC Chemokine Receptor 5 mRNA, GenBank Accession #U57840). Heterozygous individuals, carrying a 32 bp deletion in one of their two alleles, are believed to be partially resistant to HIV infection. Homozygous individuals, carrying the deletion in both alleles are believed to be immune to HIV infection.

Two oligonucleotide primer pairs for PCR were designed, using OLIGO ver. 5.0 primer analysis software (National Biosciences, Inc., Minn.), to amplify the region spanning the CKR5 32 bp deletion site. One pair selected amplified a 185 bp PCR product, while the second primer pair amplified a 148 bp PCR product in a wild type allele. Both sets of primers worked well for amplification. Since discriminating between normal and mutated alleles was more certain using the 148 bp amplicon, its primer pair was selected for the continuation of the experiment. Primer #1 is designated SEQ ID NO:1 and primer #2 is designated SEQ ID NO:2 (see FIG. 6).

Each of the 148 samples were amplified on an MJ Research Thermal Cycler using the following protocol: 25 μL PCR mixture consisting of 3 μL DNA sample, 25 pmol of each primer, and all other standard components as recommended by Perkin Elmer. The cycles used were: 94° C. for 30 seconds followed by 65° C. for 1 minute, repeated 30 times.

Figure 7:
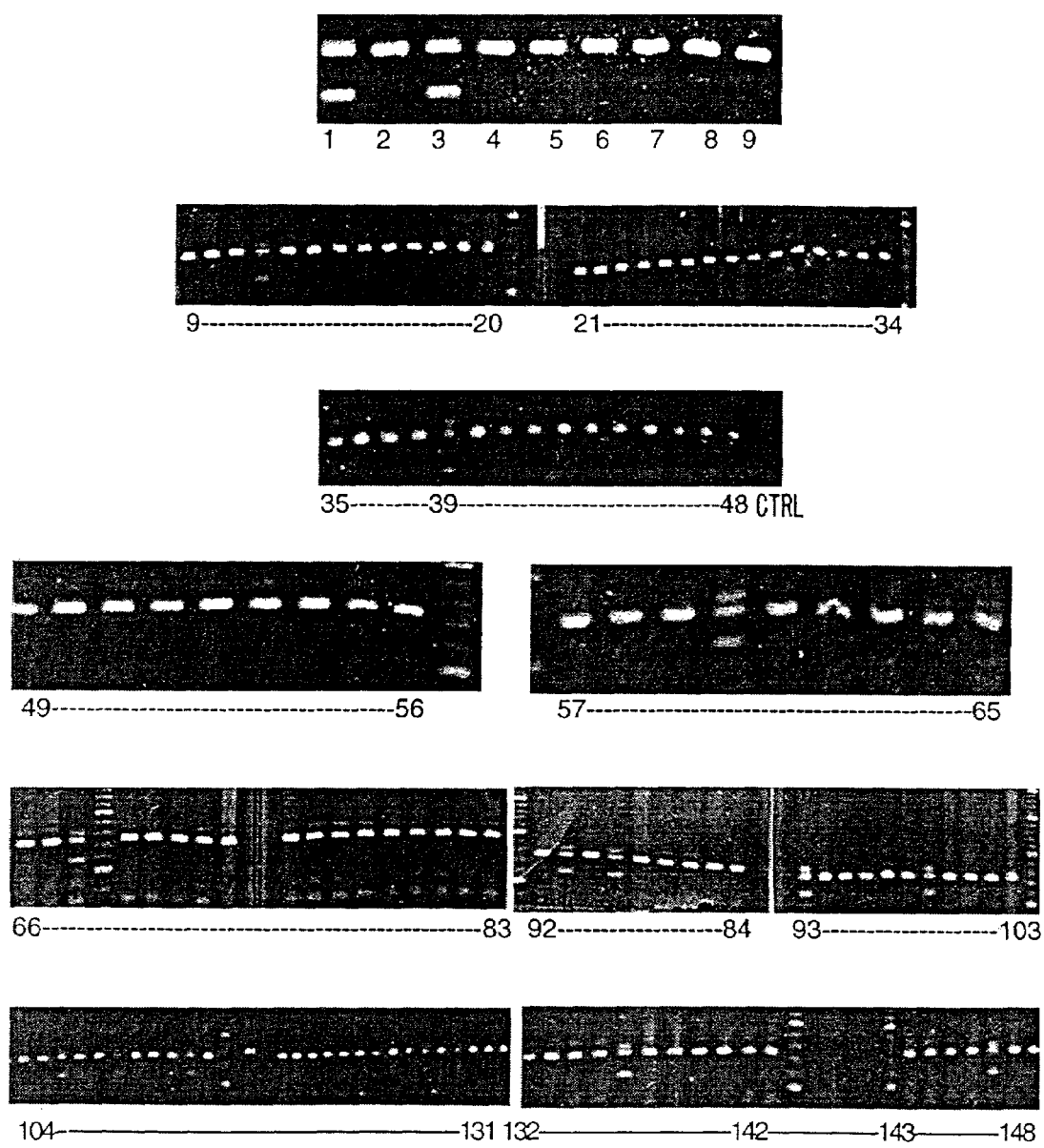
FIG. 7 is a photographic representation of agarose gels of the PCR products amplified with SEQ ID NO:1 and 2. Total DNA was purified from Orasure® pads. Lanes 1-98, HIV-1 negative samples. Lanes 99-148, HIV-1 positive samples. PCR conditions are described in Example 7.

The results of the CKR5 gene test of the 148 pads are presented in FIG. 7. The DNA quantities recovered from each pad is presented in Table 4. The average quantity of DNA extracted from a pad was 1.69+/−1.37 μg. All of the preparations, including those with the lowest yields, produced the desired results. Of the 148 samples tested, 17 heterozygotes (+/−Δ32 were found). The remaining 131 samples were wild type (+/+). No homozygotes (Δ32/Δ32) were found in the sample group.

TABLE 4

Detection of CKR5 Gene by PCR

| Patient # | Vial lot # | DNA (μg/mL) | Total Vol. (mL) | DNA/pad (μg) | Heterozygote |
|---|---|---|---|---|---|
| 42603 | v140-3 | 42 | 0.04 | 1.68 | Yes |
| 42606 | v140-3 | 17 | 0.04 | 0.68 | |
| 42607 | v140-3 | 33 | 0.04 | 1.32 | Yes |
| 42608 | v140-3 | 35 | 0.04 | 1.4 | |
| 42612 | v140-3 | 16 | 0.04 | 0.64 | |
| 42613 | v140-3 | 16 | 0.04 | 0.64 | |
| 42615 | v140-3 | 36 | 0.04 | 1.44 | |
| 42616 | v140-3 | 62 | 0.04 | 2.48 | |
| 42617 | v140-3 | 37 | 0.02 | 1.48 | |
| 42618 | v140-3 | 50 | 0.02 | 2 | |
| 42637 | v140-3 | 48 | 0.02 | 1.92 | |
| 42638 | v140-3 | 13 | 0.02 | 0.52 | Yes |
| 42639 | v140-3 | 13 | 0.02 | 0.52 | |
| 42641 | v140-3 | 30 | 0.02 | 1.2 | |
| 42657 | v140-3 | 21 | 0.02 | 0.84 | |
| 42673 | v137-4 | 11 | 0.02 | 0.44 | |
| 42683 | v137-4 | 25 | 0.02 | 1 | |
| 42804 | v137-4 | 10 | 0.02 | 0.4 | |
| 42806 | v137-4 | 34 | 0.02 | 1.36 | |
| 42807 | v137-4 | 30 | 0.02 | 1.2 | |
| 42809 | v137-4 | 23 | 0.02 | 0.92 | |
| 42810 | v137-4 | 33 | 0.02 | 1.32 | |
| 42811 | v137-4 | 37 | 0.02 | 1.48 | |
| 42812 | v137-4 | 17 | 0.02 | 0.68 | |
| 42813 | v137-4 | 42 | 0.02 | 1.68 | |
| 42816 | v137-4 | 24 | 0.02 | 0.96 | |
| 42817 | v137-4 | 23 | 0.02 | 0.92 | |
| 42818 | v137-4 | 153 | 0.02 | 6.12 | |
| 42820 | v137-4 | 53 | 0.02 | 2.12 | |
| 42822 | v137-4 | 25 | 0.02 | 1 | |
| 42823 | v137-4 | 33 | 0.02 | 1.32 | |
| 42824 | v137-4 | 85 | 0.02 | 3.4 | |
| 42825 | v137-4 | 6 | 0.02 | 0.24 | |
| 42826 | v137-4 | 18 | 0.02 | 0.72 | |
| 42828 | v137-4 | 15 | 0.02 | 0.6 | |
| 42829 | v137-4 | 15 | 0.02 | 0.6 | |
| 42831 | v137-4 | 52 | 0.02 | 2.08 | |
| 42832 | v137-4 | 83 | 0.02 | 3.32 | |
| 42835 | v137-4 | 48 | 0.02 | 1.92 | Yes |
| 42836 | v137-4 | 22 | 0.02 | 0.88 | |
| 42837 | v137-4 | 6 | 0.02 | 0.24 | |
| 42840 | v137-4 | 15 | 0.02 | 0.6 | |
| 42843 | v137-4 | 42 | 0.02 | 1.98 | |
| 42845 | v137-4 | 14 | 0.02 | 0.56 | |
| 42850 | v137-4 | 20 | 0.02 | 0.8 | |
| 42853 | v137-4 | 58 | 0.02 | 2.32 | |
| 42857 | v137-4 | 13 | 0.02 | 0.52 | |
| 42858 | v137-4 | 19 | 0.02 | 0.76 | |
| 42859 | v137-4 | 16 | 0.02 | 0.64 | |
| 42860 | v137-4 | 38 | 0.02 | 1.52 | |
| 42869 | v137-4 | 16 | 0.02 | 0.64 | |
| 42870 | v137-4 | 11 | 0.02 | 0.44 | |
| 42871 | v137-4 | 18 | 0.02 | 0.72 | |
| 42872 | v137-4 | 35 | 0.02 | 1.4 | |
| 42874 | v137-4 | 14 | 0.02 | 0.56 | |
| 42875 | v137-4 | 17 | 0.02 | 0.68 | |
| 42876 | v137-4 | 32 | 0.02 | 1.28 | |
| 42877 | v137-4 | 19 | 0.02 | 0.76 | |
| 42878 | v137-4 | 51 | 0.02 | 2.04 | |
| 42879 | v137-4 | 25 | 0.02 | 1 | Yes |
| 42880 | v137-4 | 35 | 0.02 | 1.4 | |
| 42881 | v137-4 | 9 | 0.02 | 0.36 | |
| 42882 | v137-4 | 72 | 0.02 | 2.88 | |
| 42883 | v137-4 | 19 | 0.02 | 0.76 | |
| 42884 | v140-3 | 8 | 0.02 | 0.32 | |
| 42885 | v140-3 | 21 | 0.02 | 0.84 | |
| 42887 | v140-3 | 23 | 0.02 | 0.92 | |
| 42888 | v140-3 | 47 | 0.02 | 1.88 | |
| 42889 | v140-3 | 21 | 0.02 | 0.84 | Yes |
| 42893 | v140-3 | 40 | 0.02 | 1.6 | |
| 42894 | v140-3 | 61 | 0.02 | 2.44 | |
| 42895 | v140-3 | 74 | 0.02 | 2.96 | |
| 42896 | v140-3 | 21 | 0.02 | 0.84 | |
| 42899 | v140-3 | 272 | 0.02 | 10.88 | |
| 42904 | v140-3 | 89 | 0.02 | 3.56 | |
| 42906 | v140-3 | 16 | 0.02 | 0.64 | |
| 42911 | v140-3 | 25 | 0.02 | 1 | |
| 42913 | v140-3 | 28 | 0.02 | 1.12 | |
| 42915 | v140-3 | 57 | 0.02 | 2.28 | |
| 42916 | v140-3 | 14 | 0.02 | 0.56 | |
| 42917 | v140-3 | 30 | 0.02 | 1.2 | |
| 42918 | v140-3 | 17 | 0.02 | 0.68 | |
| 42920 | v140-3 | 23 | 0.02 | 0.92 | |
| 42921 | v140-3 | 18 | 0.02 | 0.72 | |
| 42922 | v140-3 | 43 | 0.02 | 1.72 | |
| 42923 | v140-3 | 22 | 0.02 | 0.88 | |
| 42924 | v140-3 | 15 | 0.02 | 1.6 | |
| 42925 | v140-3 | 86 | 0.02 | 3.44 | |

TABLE 4-continued

Detection of CKR5 Gene by PCR

| Patient # | Vial lot # | DNA (µg/mL) | Total Vol. (mL) | DNA/pad (µg) | Heterozygote |
|---|---|---|---|---|---|
| 42926 | v140-3 | 30 | 0.02 | 1.2 | Yes |
| 42927 | v140-3 | 39 | 0.02 | 1.56 | |
| 42928 | v140-3 | 23 | 0.02 | 0.92 | Yes |
| 42934 | v140-3 | 51 | 0.02 | 2.04 | |
| 42936 | v140-3 | 75 | 0.02 | 3 | Yes |
| 42942 | v140-3 | 11 | 0.02 | 0.44 | |
| 42943 | v140-3 | 5 | 0.02 | 0.2 | |
| 42944 | v140-3 | 15 | 0.02 | 0.6 | |
| 42946 | v140-3 | 18 | 0.02 | 0.72 | |
| 42951 | v140-3 | 45 | 0.02 | 1.8 | |
| 42417 | v142-5 | 44 | 0.02 | 1.76 | Yes |
| 42418 | v142-5 | 60 | 0.02 | 2.4 | |
| 42419 | v140-3 | 57 | 0.02 | 2.28 | |
| 42369 | v137-4 | 29 | 0.02 | 1.16 | |
| 42427 | v140-3 | 123 | 0.02 | 4.92 | |
| 42381 | v137-4 | 72 | 0.02 | 2.88 | |
| 42402 | v142-5 | 80 | 0.02 | 3.2 | |
| 42377 | v137-4 | 40 | 0.02 | 1.6 | |
| 42431 | v140-3 | 37 | 0.02 | 1.48 | |
| 42434 | v140-3 | 31 | 0.02 | 1.24 | Yes |
| 42366 | v137-4 | 53 | 0.02 | 2.12 | |
| 42373 | v137-4 | 51 | 0.02 | 2.04 | |
| 42374 | v137-4 | 65 | 0.02 | 2.6 | Yes |
| 42416 | v142-5 | 75 | 0.02 | 3 | |
| 42420 | v140-3 | 87 | 0.02 | 3.48 | |
| 42398 | v142-5 | 106 | 0.02 | 4.24 | |
| 42384 | v137-4 | 51 | 0.02 | 2.04 | Yes |
| 42382 | v137-4 | 85 | 0.02 | 3.4 | |
| 42368 | v137-4 | 24 | 0.02 | 0.96 | |
| 42385 | v142-5 | 78 | 0.02 | 3.12 | |
| 42379 | v137-4 | 38 | 0.02 | 1.52 | |
| 42440 | v140-3 | 65 | 0.02 | 2.6 | |
| 42439 | v140-3 | 22 | 0.02 | 0.88 | |
| 42436 | v140-3 | 72 | 0.02 | 2.88 | |
| 42378 | v137-4 | 6 | 0.02 | 0.24 | |
| 42430 | v140-3 | 74 | 0.02 | 2.96 | |
| 42442 | v140-3 | 35 | 0.02 | 1.4 | |
| 42433 | v140-3 | 60 | 0.02 | 2.4 | Yes |
| 42432 | v140-3 | 44 | 0.02 | 1.76 | |
| 42380 | v137-4 | 30 | 0.02 | 1.2 | Yes |
| 42363 | v137-4 | 71 | 0.02 | 2.84 | |
| 42406 | v142-5 | 93 | 0.02 | 3.72 | |
| 42407 | v142-5 | 154 | 0.02 | 6.16 | |
| 42371 | v137-4 | 37 | 0.02 | 1.48 | |
| 42355 | v137-4 | 23 | 0.02 | 0.92 | |
| 42802 | v137-4 | 55 | 0.02 | 2.2 | |
| 42801 | v137-4 | 23 | 0.02 | 0.92 | |
| 42400 | v142-5 | 42 | 0.02 | 1.68 | Yes |
| 42396 | v142-5 | 71 | 0.02 | 2.84 | |
| 42387 | v142-5 | 56 | 0.02 | 2.24 | |
| 42841 | v137-4 | 103 | 0.02 | 4.12 | |
| 42839 | v137-4 | 51 | 0.02 | 2.04 | |
| 42837 | v137-4 | 16 | 0.02 | 0.64 | |
| 42827 | v137-4 | 43 | 0.02 | 1.72 | |
| 42803 | v137-4 | 39 | 0.02 | 1.56 | |
| 42848 | v137-4 | 42 | 0.02 | 1.68 | |
| 42847 | v137-4 | 18 | 0.02 | 0.72 | |
| 42846 | v137-4 | 41 | 0.02 | 1.64 | |
| 42844 | v137-4 | 67 | 0.02 | 2.68 | Yes |
| 42842 | v137-4 | 132 | 0.02 | 5.28 | |
| Average | | 42.257 | | 1.690 | |
| Standard Deviation | | | | 1.366 | |
| Median | | | | 1.4 | |

8. Example 8

Collection and Assaying Oral Fluids for Cannabinoids.

Tetrahydrocannabinol (THC) and its metabolites appear in oral fluid shortly after use, and depending upon pH and rate of saliva flow, persist in saliva for as long as 14 hours. After smoking marijuana, oral fluids may contain THC and three metabolites; $\Delta^9$-THC, cannabidiol, and 11-hydroxy-$\Delta^9$-THC. THC and its metabolites appear to be sequestered in the buccal cavity during smoking, rather than passing from the blood into the oral fluid.

The STC Technologies Cannabinoids Micro-Plate EIA kit was used to measure the cannabinoids. The 96 test kit contains:

| Kit Components | Minimum Quantity |
|---|---|
| Micro-Plate: Rabbit anti-cannabinoids immobilized on a polystyrene plate supplied in dry form | 1 |
| Enzyme Conjugate: Horseradish peroxidase labeled with a $\Delta^9$-THC derivative diluted in a protein matrix with stabilizers | 20 mL |
| Substrate Reagent: One bottle containing 3,3',5,5' tetramethylbenzidine | 20 mL |
| Stopping Reagent: 2 N sulfuric acid | 20 mL |
| STC Negative Calibrator: EpiScreen™ Control Matrix tested to be negative for THC | 4 mL |
| STC Cannabinoids Negative Control: EpiScreen™ Control Matrix containing 10 ng/mL (±3 ng/mL) $\Delta^9$-THC and tested by GC/MS | 4 mL |
| STC Cannabinoids Cutoff Calibrator: EpiScreen™ Control Matrix containing 40 ng/mL (±10%) $\Delta^9$-THC and tested by GC/MS | 4 mL |
| STC Cannabinoids Positive Control: EpiScreen™ Control Matrix containing 100 ng/mL (±10%) $\Delta^9$-THC and tested by GC/MS | 4 mL |

To the microtiter plate, 90 µL of water was added to each well. 10 µL of sample, calibrator or control was added to each well. 100 µL of enzyme conjugate was added to the well.

The plate was incubated for 30 minutes at room temperature. The wells were washed six times with 200 µL of distilled water. 100 µL of substrate was added to each well and the plate incubated at room temperature for 30 minutes in the dark. 100 µL of 2 N sulfuric acid was added to each well to stop the enzymatic activity. The absorbance at 450 and 630 nm was measured within 15 minutes of adding the sulfuric acid. The concentration of cannabinoids in the oral fluid samples was determined by comparison of the absorbances of the calibrators and controls.

To determine the THC metabolites measured by the STC Cannabinoids Micro-Plate EIA, EPISCREEN™ Oral Collection Devices were spiked with various concentrations of chemically synthesized metabolites of $\Delta^9$-THC or with $\Delta^9$-THC and its metabolites.

TABLE 5

| Compound | Tested Concentration (ng/mL) | $\Delta^9$-THC Equivalents (ng/mL) | Cross-Reactivity (%) |
|---|---|---|---|
| Cannabidiol | 100 | 51.4 | 51.4 |
| $\Delta^8$-THC | 100 | 64.1 | 64.1 |
| Cannabinol | 10,000 | 35.2 | 0.4 |
| 1-9-carboxy-11-nor-$\Delta^9$-THC glucuronide | 1,000 | 31.0 | 3.1 |
| 11-nor-9-carboxy-THC | 10 | 37.6 | 376.3 |
| $\Delta^9$-THC | 50 | 50.0 | 100.0 |

The accuracy of the collection of oral fluid and the STC Cannabinoid Micro-Plate EIA was determined by testing specimens from volunteers. The cutoffs for EIA and GC/MS were 40 ng/mL and 5 ng/mL, respectively, for EPISCREEN™ oral fluid specimens. The cutoff for EIA and GC/MS was 50 ng/mL and 15 ng/mL, respectively, for urine specimens. The EIA measures a number of THC metabolites while GC/MS is specific for $\Delta^9$-THC. For this reason, different screening and confirmation cutoffs are used to assess clinical accuracy.

Three volunteers smoked two 2.57% marijuana cigarettes or one 2.57% and one placebo cigarette. A total of forty-five oral fluid specimens and forty-three urine specimens were collected over 48 to 216 hours after smoking the last cigarette. Oral fluid samples were collected with the EPISCREEN™ Oral Collection Device (Epitope, Inc.) and tested using a Cannabinoid Micro-Plate EIA (STC Technologies).

To collect the oral fluid samples, the collection device was placed in contact with the gingival mucosa (between the lower gum and cheek) for 2-4 minutes. The collection device was placed in the accompanying Specimen Vial. To process the sample, the vial was held upright with the tip pointed up. The vial was tapped to remove the pad from the tip if necessary. The pointed end of the tip was broken off and the vial inverted into a centrifuge tube. The centrifuge tube was centrifuged at 600-800×g for 15 minutes. The extract was collected into the centrifuge tube and stored until assayed.

The results of the comparison study are presented in tabular form.

TABLE 6

Oral fluid-based EIA v. GC/MS

| | | GC/MS (5 ng/mL cutoff) | | | |
|---|---|---|---|---|---|
| Assay result | | + | − | % Sensitivity | % Specificity |
| EIA (40 ng/mL cutoff) | + | 10 | 5 | 100 | 86 |
| | − | 0 | 30 | | |

TABLE 7

Urine-based EIA v. Oral fluid-based EIA

| | | Urine EIA (50 ng/mL cutoff) | | | |
|---|---|---|---|---|---|
| Assay result | | + | − | % Sensitivity | % Specificity |
| Oral fluid EIA (40 ng/mL cutoff) | + | 9 | 5 | 28 | 62 |
| | − | 23 | 8 | | |

TABLE 8

Urine-based EIA v. Urine-based GC/MS

| | | Urine GC/MS (15 ng/mL cutoff) | | | |
|---|---|---|---|---|---|
| Assay result | | + | − | % Sensitivity | % Specificity |
| Urine EIA (50 ng/mL cutoff) | + | 23 | 2 | 92 | 94 |
| | − | 1 | 17 | | |

Poor agreement was found between the EIA of oral fluid samples and the EIA of urine samples. This is most likely due to differences in the metabolism of THC and partitioning in oral fluid and urine. THC and its metabolites, primarily $\Delta^9$-THC, generally appear later in urine and persist for up to 30 days depending upon the frequency of use. Conversely, THC in saliva is not detectable after 14 hours. The oral fluid based EIA uses THC as the analyte while the urine-based EIA employs $\Delta^9$-THC as the target analyte. Another difference is that the oral fluid-based assay was done with a polyclonal antibody whereas the urine based assay used a monoclonal antibody.

Example 9

Collection and Assaying of Cocaine in Oral Fluid Samples

Cocaine and its metabolites, benzoylecgonine (BE) and ecgonine methyl ester (EME), can be detected in oral fluid following intravenous administration. Moreover, cocaine enters the salivary glands via the blood circulation and is not present merely as residue following oral or nasal self-administration. Quantitative assessment of the excretory pattern of salivary cocaine by GC/MS in controlled-dose studies has revealed that the amount of cocaine in oral fluid consistently exceeds plasma concentrations measured concomitantly. In addition, pharmacokinetic studies have shown that cocaine appears in the oral fluid almost immediately following intravenous administration, while BE and EME are only detected at later times and in lower concentrations. A study conducted by Cone showed that, after 30 hours following cocaine administration to a single individual, the approximate ratio of cocaine:BE:EME was 19:1:1 (Cone, *Saliva Testing for Drugs of Abuse*, Addiction Research Center, National Institute on Drug Abuse, Baltimore, Md. (1992)). However additional data regarding the relative quantities of cocaine, BE and EME is limited; sufficient studies to provide an accurate approximation of the ratios of these compounds in oral fluid have not been conducted.

The STC Technologies Cocaine Metabolite Micro-Plate EIA kit was used to measure cocaine and its metabolites. The 96 test kit contains:

| Kit Components | Minimum Quantity |
|---|---|
| Micro-Plate: Rabbit anti-benzoylecgonine immobilized on a polystyrene plate supplied in dry form | 1 |
| Enzyme Conjugate: Horseradish peroxidase labeled with a benzoylecgonine derivative | 20 mL |
| Conjugate Diluent: Protein matrix of bovine serum with protein stabilizers | 20 mL |
| Substrate Reagent: One bottle containing 3,3',5,5' tetramethylbenzidine | 20 mL |
| Stopping Reagent: 2 N sulfuric acid | 20 mL |
| STC Negative Calibrator: EpiScreen ™ Control Matrix tested to be negative for benzoylecgonine | 4 mL |
| STC Cocaine Metabolite Negative Control: EpiScreen ™ Control Matrix containing 5 ng/mL benzoylecgonine | 4 mL |
| STC Cocaine Metabolite Cutoff Calibrator: EpiScreen ™ Control Matrix containing 10 ng/mL (±3 ng/mL) benzoylecgonine and tested by GC/MS | 4 mL |
| STC Cocaine Metabolite Positive Control: EpiScreen ™ Control Matrix containing 50 ng/mL (±10%) benzoylecgonine and tested by GC/MS | 4 mL |

50 μL of sample, calibrator or control was added to each well of the microtiter plate. 100 μL of enzyme conjugate was added to the well. The plate was incubated for 30 minutes at room temperature in the dark. The wells were washed six times with 300 μL of distilled water. 100 μL of substrate was added to each well and the plate incubated at room temperature for 30 minutes in the dark. 100 μL of 2 N sulfuric acid was added to each well to stop the enzymatic activity. The absorbance at 450 and 630 nm was measured within 15 minutes of adding the sulfuric acid. The concentration of cocaine in the oral fluid samples was determined by comparison of the absorbances of the calibrators and controls.

To determine the cocaine metabolites that were measured by the STC Cocaine Metabolite Micro-Plate EIA, EPISCREEN™ Oral Collection Devices were spiked with various concentrations of chemically synthesized metabolites of benzoylecgonine or with benzoylecgonine and its metabolites.

TABLE 9

| Compound | Tested Concentration (ng/mL) | Benzoylecgonine Equivalents (ng/mL) | Cross-Reactivity (%) |
|---|---|---|---|
| Cocaethylene | 100 | 13.8 | 13.8 |
| Cocaine | 100 | 12.9 | 12.9 |
| Ecgonine | 1,000 | 22.0 | 2.2 |
| Ecgonine Methyl Ester | 10,000 | 17.5 | 0.2 |
| Benzoylecgonine | 10 | 10 | 100.0 |

The accuracy of the collection of oral fluid and the STC Cocaine Metabolite Micro-Plate EIA was determined by testing specimens from chronic cocaine users as well as patients receiving a single dose. Calculations are divided into two groups as shown below. Comparable data was seen for both groups. The amount of cocaine used by chronic users in Study 1 could not be accurately determined since specimens were collected at a drug rehabilitation center. The cutoffs for EIA and GC/MS were 10 ng/mL for EpiScreen™ specimens. For urine specimens, the EIA cutoff was 300 ng/mL per the EIA package insert and the GC/MS cutoff was 150 ng/mL. These studies demonstrate that the STC EIA can effectively detect cocaine and cocaine metabolites in oral fluid and urine-based specimens.

Study 1: Chronic Cocaine Users

A total of 149 subjects participated in the clinical study. Matched urine and EpiScreen™ specimens were collected from each subject and were tested in the STC Cocaine Metabolite Micro-Plate EIA according to product insert. Specimens were confirmed by GC/MS analysis.

To collect the oral fluid samples, the collection device was placed in contact with the gingival mucosa (between the lower gum and cheek) for 2-4 minutes. The collection device was placed in the accompanying Specimen Vial. To process the sample, the vial was held upright with the tip pointed up. The vial was tapped to remove the pad from the tip if necessary. The pointed end of the tip was broken off and the vial inverted into a centrifuge tube. The centrifuge tube was centrifuged at 600 -800×g for 15 minutes. The extract was collected into the centrifuge tube and stored until assayed.

The results of the comparison study are presented in tabular form.

TABLE 10

Oral fluid-based EIA v. GC/MS

| | | GC/MS | | | |
|---|---|---|---|---|---|
| | Assay result | + | – | % Sensitivity | % Specificity |
| EIA | + | 43 | 22 | 94 | 79 |
| | – | 3 | 81 | | |

TABLE 11

Urine-based EIA v. Oral fluid-based EIA

| | | Urine EIA | | | |
|---|---|---|---|---|---|
| | Assay result | + | – | % Sensitivity | % Specificity |
| Oral fluid EIA | + | 59 | 6 | 75 | 91 |
| | – | 20 | 64 | | |

TABLE 12

Urine-based EIA v. Urine-based GC/MS

| | | Urine GC/MS | | | |
|---|---|---|---|---|---|
| | Assay result | + | – | % Sensitivity | % Specificity |
| Urine EIA (50 ng/mL cutoff) | + | 79 | 0 | 96 | 100 |
| | – | 3 | 67 | | |

Study 2: Single Dose Study

A total of 10 volunteers received 10 or 25 mg of intravenous cocaine in a controlled environment. Oral fluid and urine specimens were collected over 0-130 hours after dose. Oral fluid specimens (400 .mu.L) were added to the collection pad and diluted into the EPISCREEN™ Control Matrix. Samples were then tested using the STC assay and GC/MS. The results were platted over time for each patient. The oral fluid and urine results were compared using similar points on the curve. For all volunteers, regardless of the dose, the cocaine concentrations in oral fluid were detectable 5 minutes after dosing. For the subject who received 10 mg, oral fluid cocaine levels were no longer detectable after 25 minutes. For the remaining nine subjects who received 25 mg intravenous cocaine, drug levels in oral fluids were detectable after dosing for up to 3-6 hours. The length of time detectable drug concentrations were present in urine varied greatly. In some subjects, a negative result was seen for samples obtained earlier in the study while samples obtained later in the study would give positive results. This variability could be attributed to a number of factors, including the volume of urine collected and the sensitivity of the cutoff used. In general, however, positive results were obtained in the subjects for up to 58 hours after dosing. The accuracy results are shown below.

TABLE 13

Oral fluid-based EIA v. GC/MS

| | | GC/MS | | | |
|---|---|---|---|---|---|
| | Assay result | + | – | % Sensitivity | % Specificity |
| EIA | + | 89 | 9 | 96 | 87 |
| | – | 4 | 61 | | |

TABLE 14

Urine-based EIA v. Oral fluid-based EIA

| | | Urine EIA | | | |
|---|---|---|---|---|---|
| | Assay result | + | – | % Sensitivity | % Specificity |
| Oral fluid EIA | + | 83 | 11 | 72 | 73 |
| | – | 32 | 30 | | |

TABLE 15

Urine-based EIA v. Urine-based GC/MS

| | | Urine GC/MS | | | |
|---|---|---|---|---|---|
| | Assay result | + | – | % Sensitivity | % Specificity |
| Urine EIA | + | 119 | 2 | 95 | 98 |
| | – | 6 | 95 | | |

10. Example 10

Collection and Assay of Methamphetamine in Oral Fluid

Methamphetamine appears in oral fluid shortly after use and depending upon dose and rate of saliva flow, has been detected in oral fluid for as long as 50 hours. The major species detected in oral fluid is methamphetamine. Methamphetamine enters the salivary glands via the blood circulation and is not present merely as residue following oral self-administration. The window of detection for methamphetamine in oral fluid is similar to that in urine. Generally, detection of methamphetamine in urine is successful for 24-48 hours following use, although the time period may extend to several days for chronic users.

Methamphetamine is partially metabolized to amphetamine and, under normal conditions, up to 43% of methamphetamine is excreted in the urine unchanged. The relative amounts of drug excreted in urine is dependent upon urinary pH, with up to 76% of methamphetamine found unchanged in acid urine and only 2% in alkaline urine. On the other hand, oral fluid pH has been shown to remain relatively constant regardless of the pH of urine.

The presence of methamphetamine and metabolites in oral fluid were detected with the STC Methamphetamine Micro-Plate EIA. The 96 test kit contains:

| Kit Components | Minimum Quantity |
|---|---|
| Micro-Plate: Rabbit anti-methamphetamine polyclonal antibody immobilized on a polystyrene plate supplied in dry form | 1 |
| Enzyme Conjugate: Horseradish peroxidase labeled with a methamphetamine hapten diluted in a protein matrix of bovine serum with protein stabilizers | 20 mL |
| Substrate Reagent: One bottle containing 3,3',5,5' tetramethylbenzidine | 20 mL |
| Stopping Reagent: 2 N sulfuric acid | 20 mL |
| STC Negative Calibrator: EpiScreen ™ Control Matrix tested to be negative for methamphetamine | 4 mL |
| STC Cocaine Metabolite Negative Control: EpiScreen ™ Control Matrix containing 5 ng/mL (±3 ng/mL) methamphetamine tested by GC/MS | 4 mL |
| STC Cocaine Metabolite Cutoff Calibrator: EpiScreen ™ Control Matrix containing 10 ng/mL (±3 ng/mL) methamphetamine and tested by GC/MS | 4 mL |
| STC Cocaine Metabolite Positive Control: EpiScreen ™ Control Matrix containing 20 ng/mL (±3 ng/mL) methamphetamine and tested by GC/MS | 4 mL |

50 µL of sample, calibrator or control was added to each well of the microtiter plate. 100 µL of enzyme conjugate was added to the well. The plate was incubated for 30 minutes at room temperature. The wells were washed six times with 300 µL of distilled water. 100 µL of substrate was added to each well and the plate incubated at room temperature for 30 minutes in the dark. 100 µL of 2 N sulfuric acid was added to each well to stop the enzymatic activity. The absorbance at 450 and 630 nm was measured within 15 minutes of adding the sulfuric acid. The concentration of cocaine in the oral fluid samples was determined by comparison of the absorbances of the calibrators and controls.

The accuracy of the collection of oral fluid and the STC Methamphetamine Micro-Plate EIA was determined by testing specimens from chronic methamphetamine users as well as patients receiving a single dose. Of the 81 individuals tested, 57 were self-reported methamphetamine users and 24 individuals were non-users. Oral fluid specimens were collected using the EPISCREEN™ Oral Specimen Collection device. The limit of quantitation (LOQ) for the detection of methamphetamine in EpiScreen.™. oral fluid by GC/MS was 1 ng/mL. Cutoff values were 10 ng/mL for EpiScreen.TM. EIA and GC/MS, 1000 ng/mL for urine EIA, and 500 ng/mL for urine GC/MS. Comparisons of EPISCREEN™ and urine EIA with GC/MS are shown below.

TABLE 16

Oral fluid-based EIA v. GC/MS

| | | GC/MS (10 ng/mL cutoff) | | | |
|---|---|---|---|---|---|
| | Assay result | + | − | % Sensitivity | % Specificity |
| EIA (10 ng/mL cutoff) | + | 42 | 0 | 100 | 100 |
| | − | 0 | 39 | | |

TABLE 17

Urine-based EIA v. Oral fluid-based EIA

| | | Urine EIA (1,000 ng/mL cutoff) | | | |
|---|---|---|---|---|---|
| | Assay result | + | − | % Sensitivity | % Specificity |
| Oral fluid EIA (10 ng/mL cutoff) | + | 39 | 3 | 95.1 | 92.5 |
| | − | 2 | 37 | | |

TABLE 18

Urine- and Oral fluid-based EIA v. Urine-based GC/MS

| | Assay result | Urine GC/MS (500 ng/mL cutoff) | | | |
|---|---|---|---|---|---|
| | | + | − | % Sensitivity | % Specificity |
| Oral fluid EIA (10 ng/mL cutoff) | + | 39 | 3 | 97.5 | 92.7 |
| | − | 1 | 38 | | |
| Oral Fluid GC/MS (10 ng/mL cutoff) | + | 39 | 3 | 97.5 | 92.7 |
| | − | 1 | 38 | | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed:

1. A method for preparing an oral fluid sample for genomic analysis, said sample comprising diagnostic markers and cellular components, said method comprising:
    (i) collecting the oral fluid sample onto a bibulous absorbent pad having a fibrous matrix;
    (ii) impregnating the pad with an aqueous diagnostic marker releasing solution comprising a non-ionic detergent, said non-ionic detergent being able to selectively extract the diagnostic markers while preserving the cellular components within the pad for genomic analysis;
    (iii) removing the diagnostic marker releasing solution and the diagnostic markers from the pad; and
    (iv) impregnating the pad with a nucleic acid releasing solution, thereby preparing an oral fluid sample for genomic analysis.

2. The method of claim 1, wherein the nucleic acid releasing solution comprises 0.001-0.2M buffer salts with a buffering capacity of pH 6-9.

3. The method of claim 1, wherein the nucleic acid releasing solution comprises a chelating agent.

4. The method of claim 3, wherein the chelating agent is ethylenediaminetetraacetic acid (EDTA) at a concentration of about 0.05-0.15 M.

5. The method of claim 1, wherein the nucleic acid releasing solution comprises a detergent capable of lysing whole cells.

6. The method of claim 5, wherein the detergent is sodium dodecyl sulfate (SDS) in a concentration of about 0.2-1%.

7. The method of claim 1, wherein the nucleic acid releasing solution comprises a proteinase.

8. The method of claim 7, wherein the proteinase is Proteinase K at a concentration of about 50-150 μg/mL.

9. The method of claim 1, further comprising extracting the cellular components from the bibulous absorbent pad.

10. The method of claim 1, wherein the oral fluid sample comprises mucosal transudate.

11. The method of claim 1, wherein the oral fluid sample comprises buccal cells.

12. The method of claim 1, wherein the oral fluid sample comprises saliva.

13. The method of claim 1, wherein said non-ionic detergent is TWEEN-20.

14. The method of claim 1, wherein the bibulous pad further comprises an antimicrobial agent.

15. The method of claim 14, wherein the antimicrobial agent is chlorhexidine digluconate.

16. The method of claim 1, wherein said aqueous diagnostic marker releasing solution comprises a preservative.

17. The method of claim 1, wherein said non-ionic detergent is Triton X-100.

18. The method of claim 1, wherein said non-ionic detergent is Nonidet P-40.

19. The method of claim 1, wherein the concentration of said non-ionic detergent is 0.01 to 1%.

20. The method of claim 5, wherein said detergent is an ionic detergent.

21. The method of claim 5, wherein said detergent is selected from the group consisting of: hexadecyltrimethylammonium bromide (CTAB), guanidine hydrochloride, and guanidinium thicyanate.

22. A method for preparing an oral fluid sample for genomic analysis, said sample comprising cellular components, said method comprising:
 (i) collecting the oral fluid sample onto a bibulous absorbent pad having a fibrous matrix;
 (ii) impregnating the pad with a nucleic acid releasing solution; and
 (iii) removing nucleic acid from the pad, thereby preparing an oral fluid sample for genomic analysis.

23. The method of claim 22, further comprising amplifying the nucleic acid removed from the pad.

* * * * *